(12) United States Patent
Hancock et al.

(10) Patent No.: US 9,474,730 B2
(45) Date of Patent: Oct. 25, 2016

(54) METHODS AND COMPOSITIONS FOR USE WITH K-RAS MEDIATED DISORDERS

(71) Applicant: Board of Regents of the University of Texas System, Austin, TX (US)

(72) Inventors: John F. Hancock, Houston, TX (US); Dharini Van Der Hoeven, Houston, TX (US); Kwang-Jin Cho, Houston, TX (US)

(73) Assignee: BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 482 days.

(21) Appl. No.: 13/873,799

(22) Filed: Apr. 30, 2013

(65) Prior Publication Data

US 2013/0296438 A1 Nov. 7, 2013

Related U.S. Application Data

(60) Provisional application No. 61/640,451, filed on Apr. 30, 2012.

(51) Int. Cl.
| | |
|---|---|
| *A61K 31/135* | (2006.01) |
| *A01N 33/02* | (2006.01) |
| *C07C 211/00* | (2006.01) |
| *A61K 31/137* | (2006.01) |
| *C12Q 1/48* | (2006.01) |
| *G01N 33/50* | (2006.01) |
| *A61K 45/06* | (2006.01) |

(52) U.S. Cl.
CPC ............. *A61K 31/137* (2013.01); *A61K 45/06* (2013.01); *C12Q 1/485* (2013.01); *G01N 33/5011* (2013.01); *G01N 2333/82* (2013.01)

(58) Field of Classification Search
CPC .... A61K 31/137; A61K 45/06; C12Q 1/485; G01N 2333/82; G01N 33/5011
USPC ........................................... 514/648; 564/316
See application file for complete search history.

(56) References Cited

U.S. PATENT DOCUMENTS

| | | | |
|---|---|---|---|
| 8,883,841 B2 * | 11/2014 | Fang .............................. | 514/415 |
| 2010/0136138 A1 * | 6/2010 | Kloog et al. .................. | 424/649 |
| 2015/0344407 A1 * | 12/2015 | Hancock ............... | C07C 215/08 514/539 |

FOREIGN PATENT DOCUMENTS

WO   WO 2009/148623 A2 * 12/2009   ........... A61K 31/445

OTHER PUBLICATIONS

Hoeven et al., Fendiline inhibits K-Ras plasma membrane localization and blocks K-Ras signal transmission, Mol. Cell. Biol., 1-52, Nov. 5, 2012.*

* cited by examiner

*Primary Examiner* — My-Chau T Tran
(74) *Attorney, Agent, or Firm* — Conley Rose, P.C.

(57) ABSTRACT

Methods and compositions that can be used to identify and characterize inhibitors of K-ras localization to the plasma membrane and in doing so inhibit the signal transduction of K-ras. Such compositions can be used to treat K-ras mediated disorders, such as cancer.

5 Claims, 12 Drawing Sheets

METHODS AND COMPOSITIONS FOR USE WITH K-RAS MEDIATED DISORDERS

CROSS-REFERENCE TO RELATED APPLICATIONS

This application claims the benefit of U.S. Patent Application Ser. No. 61/640,451, filed Apr. 30, 2012, which is hereby incorporated by reference in its entireties for all purposes.

FIELD OF THE INVENTION

This disclosure generally relates to methods of inhibiting k-Ras signaling; blocking the association of a K-ras protein with a plasma membrane and providing methods of treating K-ras mediated disorders in a patient in need thereof. Further methods are provided that may be used to identify compounds that block the association of a K-ras protein with a plasma membrane, and may be further used as medicaments in treating K-ras mediated disorders.

BACKGROUND

Ras is the name given to a family of related proteins found inside cells, including human cells. All Ras protein family members belong to a class of protein called small GTPase, and are involved in transmitting signals within cells (cellular signal transduction). All Ras proteins are related in 3D structure and regulate diverse cell behaviors.

When Ras is 'switched on' by incoming signals, it subsequently switches on other proteins, which turn on genes involved in cell growth, differentiation and survival. As a result, mutations in ras genes can lead to the production of permanently activated Ras proteins. This can cause inappropriate and overactive signaling inside the cell, even in the absence of incoming signals, which may permanently turn on genes involved in cell growth, differentiation and survival. As a result, mutations in ras genes can lead to the production of permanently activated Ras proteins.

Overactive Ras signaling can ultimately lead to cancer. Ras is the most common oncogene in human cancer—mutations that permanently activate Ras are found in 15% of all human tumors and up to 90% in certain types of cancer (e.g. pancreatic cancer). The clinically most notable members of the Ras subfamily are H-Ras, N-Ras and K-Ras, mainly for being implicated in many types of cancer. Inappropriate activation of the gene has been shown to play a key role in signal transduction, proliferation and malignant transformation.

Ras GTPases operate as molecular switches in signaling pathways that control cell proliferation. Ras normally oscillates between an active, GTP-bound and inactive GDP-bound state in a cycle that is tightly controlled by guanine nucleotide exchange factors and GTPase activating proteins. Oncogenic Ras mutations occur in ~15% of all human tumors and directly contribute to malignant transformation by locking Ras in the GTP-bound state leading to constitutive activation of downstream signaling pathways. For example, oncogenic K-ras mutations occur in 90% of pancreatic, 45% of colorectal and 35% of lung carcinomas (Bos J L. ras oncogenes in human cancer: a review. *Cancer Res.* 1989; 49 (17):4682-9 and Downward J. Targeting RAS signalling pathways in cancer therapy. *Nat Rev Cancer.* 2003; 3 (1):11-22). Many small molecule inhibitors of kinases downstream of K-ras have been developed as anti-cancer therapeutics. With the Raf-MAPK cascade, potent inhibitors of BRaf, CRaf and MEK are in clinical use (Ribas A and Flaherty K T. BRAF targeted therapy changes the treatment paradigm in melanoma. *Nat Rev Clin Oncol.* 2011; 8(7): 426-33; Kefford H A R, Brown M P, Millward M, Infante J R, Long G V, Ouellet D, Curtis M, Lebowitz P F, Falchook G S. Phase I/II study of GSK2118436, a selective inhibitor of oncogenic mutant BRAF kinase, in patients with metastatic melanoma and other solid tumors. *J. Clin. Oncol.* (Meeting Abstracts) 2010; 28, 8503; Poulikakos P I and Rosen N. Mutant BRAF melanomas—dependence and resistance. *Cancer Cell.* 2011; 19(1): 11-5; Joseph E W, Pratilas C A, Poulikakos P I, Tadi M, Wang W, Taylor B S, Halilovic E, Persaud Y, Xing F, Viale A, Tsai J, Chapman P B, Bollag G, Solit D B and Rosen N. The RAF inhibitor PLX4032 inhibits ERK signaling and tumor cell proliferation in a V600E BRAF-selective manner. *Proc Natl Acad Sci USA.* 2010; 107(33):14903-8; Flaherty K T, Puzanov I, Kim K B, Ribas A, McArthur G A, Sosman J A, O'Dwyer P J, Lee R J, Grippo J F, Nolop K and Chapman P B. Inhibition of mutated, activated BRAF in metastatic melanoma. *N Engl J Med.* 2010; 363(9):809-19; Infante J R, Fecher L A, Nallapareddy S, Gordon M S, Flaherty K T, Cox D S, DeMarini D J, Morris S R, Burris H A and Messersmith W A. Safety and efficacy results from the first-in-human study of the oral MEK 1/2 inhibitor GSK1120212. *J. Clin. Oncol.* (Meeting Abstracts) 2010; 28, 2503; Poulikakos P I and Solit D B. Resistance to MEK inhibitors: should we co-target upstream? *Sci. Signal.* 2011; 4 (166), pe16; Corcoran R B, Settleman J, and Engelman J A. Potential therapeutic strategies to overcome acquired resistance to BRAF or MEK inhibitors in BRAF mutant cancers. *Oncotarget.* 2011; 2(4): 336-346; Halilovic E and Solit D B. Therapeutic strategies for inhibiting oncogenic BRAF signaling. *Curr Opin Pharmacol.* 2008; 8(4):419-26; Greger J G, Eastman S D, Zhang V, Bleam M R, Hughes A M, Smitheman K N, Dickerson S H, Laquerre S G, Liu L, and Gilmer T M. Combinations of BRAF, MEK, and PI3K/mTOR Inhibitors Overcome Acquired Resistance to the BRAF Inhibitor GSK2118436 Dabrafenib, Mediated by NRAS or MEK Mutations. *Mol Cancer Ther.* 2012; 11 (4):909-20).

However the clinical responses to Raf inhibitors can be relatively short-lived, with treatment failure and tumor progression occurring due to acquired resistance, primarily as a result of secondary mutations in the oncogenic BRaf or other proteins such as N-ras or MEK (Whittaker S, Kirk R, Hayward R, Zambon A, Viros A, Cantarino N, Affolter A, Nourry A, Niculescu-Duvaz D, Springer C, and Marais R. Gatekeeper mutations mediate resistance to BRAF-targeted therapies. *Sci Transl Med.* 2010; 2(35):35 ra41; Nazarian R, Shi H, Wang Q, Kong X, Koya R C, Lee H, Chen Z, Lee M K, Attar N, Sazegar H, Chodon T, Nelson S F, McArthur G, Sosman J A, Ribas A, and Lo R S. Melanomas acquire resistance to B-RAF(V600E) inhibition by RTK or N-RAS upregulation. *Nature.* 2010; 468(7326):973-7; Wagle N, Emery C, Berger M F, Davis M J, Sawyer A, Pochanard P, Kehoe S M, Johannessen C M, Macconaill L E, Hahn W C, Meyerson M, and Garraway L A. Dissecting Therapeutic Resistance to RAF Inhibition in Melanoma by Tumor Genomic Profiling. *J Clin Oncol.* 2011; 29(22): 3085-96). In addition, while BRaf inhibitors inhibit the activation of BRaf/MEK/ERK in BRaf mutant cell lines, they paradoxically activate MEK/ERK signaling in cell lines with Ras mutations (Heidorn S J, Milagre C, Whittaker S, Nourry A, Niculescu-Duvas I, Dhomen N, Hussain J, Reis-Filho J S, Springer C J, Pritchard C, and Marais R. Kinase-dead BRAF and oncogenic RAS cooperate to drive tumor progression through CRAF. *Cell.* 2010; 140 (2):209-21; Hatzivassiliou G, Song K, Yen I, Brandhuber B J, Anderson D J, Alvarado R, Ludlam M J, Stokoe D, Gloor S L, Vigers G, Morales T, Aliagas I, Liu B, Sideris S, Hoeflich K P, Jaiswal B S, Seshagiri S, Koeppen H, Belvin M, Friedman L S, and Malek S. RAF inhibitors prime wild-type RAF to activate the MAPK pathway and enhance growth. *Nature.* 2010; 464 (7287):431-5; Poulikakos P I, Zhang C, Bollag G, Shokat K M, and Rosen N. RAF inhibitors transactivate RAF dimers and ERK signalling in cells with wild-type BRAF. *Nature.* 2010; 464 (7287):427-30).

Approaches to directly target the Ras protein have been unsuccessful. Ras proteins undergo post translational processing to generate a lipid modified C-terminus. The cysteine residue in the C-terminal CAAX motif of the cytosolic precursors of all three Ras isoforms is isoprenylated by farnesyl protein transferase, which facilitates endoplasmic reticulum (ER) association where the AAX motif is cleaved off by Ras-converting enzyme 1 (Rce1) followed by carboxymethylation of the farnesylated cysteine by isoprenyl cysteine transferase (Icmt) (Omerovic J, Laude A J, and Prior I A. Ras proteins: paradigms for compartmentalised and isoform-specific signalling. *Cell Mol Life Sci.* 2007; 64(19-20):2575-89). The weak membrane binding of these proteins rendered by the farnesyl moiety is further enhanced by secondary motifs or modifications, which is the basic hexalysine patch in K-ras, and one two palmitoyl groups on cysteines 181 and 184 in N- and H-ras, respectively (Apolloni A, Prior I A, Lindsay M, Parton R G, and Hancock J F. H-ras but not K-ras traffics to the plasma membrane through the exocytic pathway. *Mol Cell Biol.* 2000; 20(7):2475-87; Choy E, Chiu V K, Silletti J, Feoktistov M, Morimoto T, Michaelson D, Ivanov I E, Philips M R. Endomembrane trafficking of ras: the CAAX motif targets proteins to the ER and Golgi. *Cell.* 1999; 98(1):69-80; Hancock J F, Paterson H, and Marshall C J. A polybasic domain or palmitoylation is required in addition to the CAAX motif to localize p21ras to the plasma membrane. *Cell.* 1990; 63(1):133-9).

These second signal motifs also specify the trafficking routes: H- and N-ras traffic via the conventional secretory pathway, whilst preliminary data from yeast indicates that K-ras transits via a poorly understood Golgi-independent route that requires mitochondrial function and class C vps proteins (Apolloni, et al., 2000, ibid, Choy E, Chiu V K, Silletti J, Feoktistov M, Morimoto T, Michaelson D, Ivanov I E, and Philips M R. Endomembrane trafficking of Ras: the CAAX motif targets proteins to the ER and Golgi. *Cell.* 1999; 98(1):69-80; Wang G, and Deschenes R J. Plasma membrane localization of Ras requires class C vps proteins and functional mitochondria in *Saccharomyces cerevisiae. Mol Cell Biol.* 2006; 26(8):3243-55).

Since farnesylation is prerequisite for Ras biological activity (Hancock J F, Magee A I, Childs J E, and Marshall C J. All ras proteins are polyisoprenylated but only some are palmitoylated. *Cell.* 1989; 57(7):1167-77; Casey P J, Solski P A, Der C J and Buss J E. p21ras is modified by a farnesyl isoprenoid. *Proc Natl Acad Sci USA.* 1989; 86(21):8323-7; Rowinsky E K. Lately, it occurs to me what a long, strange trip it's been for the farnesyltransferase inhibitors. *J Clin Oncol.* 2006; 24(19):2981-4) farnesyltransferase inhibitors (FTIs) were thought to be excellent anti-Ras drugs. However, in cells treated with FTIs K- and N-ras are alternatively prenylated by geranylgeranyl transferase 1 (GGTase1) and traffic normally from the ER to the plasma membrane (Rowinsky, et al., 2006, ibid; Sebti S M, and Der C J. Opinion: Searching for the elusive targets of farnesyltransferase inhibitors. *Nat Rev Cancer.* 2003; 3(12):945-51). Geranylgeranylated oncogenic K- and N-ras are as transforming as the cognate farnesylated proteins (Hancock J F, Cadwallader K, Paterson H, and Marshall C J. A CAAX or a CAAL motif and a second signal are sufficient for plasma membrane targeting of ras proteins. *EMBO J.* 1991; 10(13): 4033-9; Cox, A. D., Hisaka, M. M., Buss, J. E. & Der, C. J., Specific isoprenoid modification is required for function of normal, but not oncogenic, Ras protein. *Mol Cell Biol* 1992; 12: 2606-15). Inhibition of the two post-prenylation enzymes Rce1 and Icmt has attracted considerable attention, as post-prenylation reactions are shared by both farnesylated and geranylgeranylated proteins. However, since Rce1 and Icmt act on more targets than the prenylation enzymes, toxicity is a concern with the post-prenylation inhibitors (Panagiotis A. Konstantinopoulos, Michalis V. Karamouzis1 & Athanasios G. Papavassiliou, *Nature Reviews Drug Discovery* 2007; 6: 541-555).

It has previously been shown that K-ras must be localized to the plasma membrane in order to activate downstream effector pathways (Hancock, J. F. Ras proteins: different signals from different locations, *Nat Rev Mol Cell Biol* 2003; 4: 373-84; Hancock, J. F. & Parton, R. G., Ras plasma membrane signaling platforms. *Biochem J.* 2005; 389: 1-11). Therefore inhibition or blocking of K-ras association with the plasma membrane would provide a much needed method of inhibiting K-ras signaling and turning off genes involved in erroneous cell growth and proliferation, and thus provide methods of treating oncogenic K-ras disorders. Thus, the present disclosure addresses such need, and provides methods that identify inhibitors of K-ras localization to the plasma membrane, and thus provide methods of inhibiting the signal transduction from oncogenic K-ras, which may be used as therapies for cancer, such as though not limited to, leukemias, colorectal cancers, pancreatic cancers and lung cancers.

BRIEF SUMMARY OF THE DISCLOSED EMBODIMENTS

The present disclosure thus relates to a method of inhibiting K-ras signaling, where inhibiting comprises blocking the association of a K-ras protein with a plasma membrane, and the blocking is by a chemical compound. In some embodiments of the method herein described, the compound is fendiline, fendiline HCl, or a combination thereof. In further embodiments of the method, the compound is substantially in R-isomeric form, in other embodiments the compound may be a racemic mixture.

In some embodiments of the method of inhibiting K-ras signaling, blocking is by a non-L-type calcium channel blocking mechanism. In other embodiments the method of inhibiting K-ras signaling is $Ca^{2+}$ independent.

In some embodiments of the method of inhibiting K-ras signaling, the compound targets a K-ras polybasic domain, in some further embodiments the compound targets a K-ras polybasic domain, where the polybasic domain is prenylated. In other embodiments the compound acts to perturb the electrostatic interactions of the polybasic domains and plasma membrane, and in further embodiments of the method the compound acts to perturbs the trafficking of prenylated polybasic domain targeted RAS proteins; and in some further embodiments of the method of inhibiting K-ras signaling, the compound reduces K-ras-plasma membrane nanoclustering; and redistributes K-ras to the endoplasmic reticulum. In other embodiments of the method, blocking increases the binding of a K-ras protein to at least one of: cytosol; endoplasmic reticulum; endosomes; or Golgi apparatus. In a still further embodiment of the method of inhibiting K-ras signaling, the compound inhibits K-ras-dependent RAF-MAPK and PI3K-AKT signaling.

In one embodiment a method of treating a K-ras mediated disorder in a patient in need thereof is provided, said method comprises: administering to the patient a therapeutically effective amount of a compound that inhibits K-ras signaling by blocking the association of the K-ras protein with the plasma membrane. In some embodiments of the method herein described the compound is fendiline; fendiline HCl or a combination thereof, and in further embodiments of the method, the compound is substantially in R-isomeric form, in other embodiments the compound may be a racemic mixture.

In a further embodiment of the method of treating a K-ras mediated disorder the compound is used in combination with at least one other chemotherapeutic compound in a combination therapy. In another embodiment of the method of treating a K-ras mediated disorder, the K-ras mediated disorder is characterized by the presence of a mutant K-ras oncogene. In a further embodiment of the method of treating a K-ras mediated disorder, the K-ras mediated disorder is undesirable or pathologic cell proliferation, and in a still further embodiment the K-ras mediated disorder is cancer, and in another embodiment the cancer is at least one of: leukemia, colorectal cancer, pancreatic cancer, or lung cancer. In some embodiments of the method of treating a K-ras mediated disorder administering to the patient is oral or intravenous, in a further embodiment said administering is oral, and by a controlled release formulation, and in still further embodiments, said patient is human or veterinary. In some embodiments of the method of treating a K-ras mediated disorder the compound inhibits K-ras-dependent RAF-MAPK and PI3K-AKT signaling.

In some embodiments a medicament comprising a therapeutically effective amount of fendiline or fendiline HCl or a combination thereof is provided, which inhibits K-ras signaling to treat a K-ras mediated disorder in a patient in need of such a treatment. In some embodiments the medicament comprises a further therapeutic compound, and in another embodiment further comprises a pharmaceutical vehicle.

The disclosure herein provides in some embodiments a method of identifying a compound that blocks the association of K-ras protein with a plasma membrane; the method comprises: a) incubating MDCK-mGFP-Target cells constructs; b) adding a test compound to said cells, and further incubating; c) imaging cells from step b); d) analyzing protein localization in cells of step c; and e) selecting based on step d) compounds that block protein localization compared to a control, wherein said compounds inhibit K-ras signaling. In some embodiments the MDCK-mGFP-Target cells are MDCK-mGFP-CTK cells, in other embodiment the MDCK-mGFP-Target cells are MDCK-mGFP-CTH cells. In further embodiments of the method of identifying a compound that blocks the association of K-ras protein with a plasma membrane, the wherein said protein is K-ras, the construct comprises K-ras protein amino acids 166-188. In a still further embodiment, wherein said protein is H-ras, the construct comprises K-ras protein amino acids 166-189.

In some embodiments of the method of identifying a compound that blocks the association of K-ras protein with a plasma membrane imaging is by a high throughput bioimager, using GFP-confocal mode, in another embodiment, step c further comprises fixing cells, prior to imaging. In other embodiments protein localization comprises re-localization of K-ras from a plasma membrane to at least one of endosomes, golgi apparatus, endoplasmic reticulum and cytosol, and in some further embodiments protein localization is further analyzed by electron microscopy.

Thus, embodiments described herein comprise a combination of features and characteristics intended to address various shortcomings associated with known methods of inhibiting K-ras signalling and providing therapeutic means for disorders characterized by a mutant K-ras oncogene, while further providing methods of identifying compounds capable of inhibiting such K-ras signaling, and treating such disorders. The various features and characteristics described above, as well as others, will be readily apparent to those skilled in the art upon reading the following detailed description, and by referring to the accompanying drawings.

DETAILED DESCRIPTION

Figure 1:
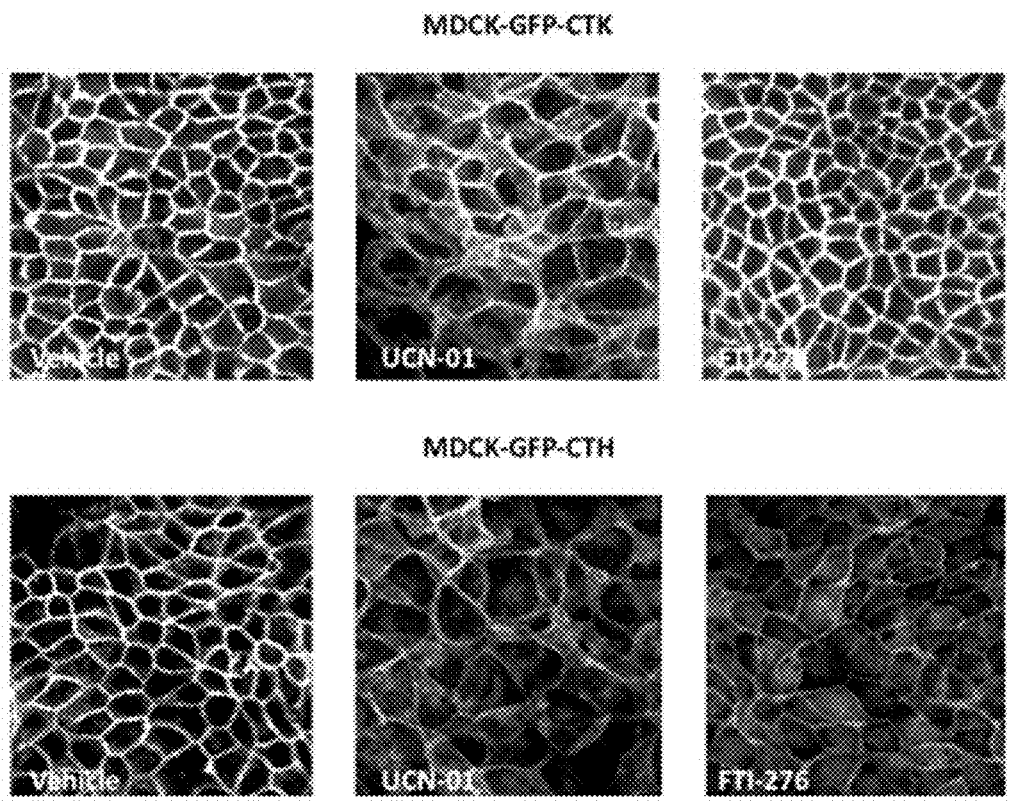
FIG. 1: Illustrates results of a high throughput cell-based screening of chemical libraries: Madin-Darby Canine Kidney epithelial cells (MDCK) expressing monomeric green fluorescent protein (mGFP)-tagged C-terminal region of K- or H-ras (GFP-CTK and GFP-CTH) were seeded in 96 well plates and treated with drug libraries for 48 h. Cells were then fixed with paraformaldehyde and imaged by BD Pathway Imager in confocal mode; shown are representative images of cells treated with vehicle, 2.5 ng/mL UCN-01, and 10 µM FTI-276; wherein experimentation was performed in accordance with principles described herein.

Embodiments herein addressed are intended to overcome certain limitations in the art for identifying compounds which are inhibitors of K-ras localization to the plasma membrane, and which in turn inhibit signal transduction from oncogenic K-ras. Methods of inhibiting signal transduction of K-ras with such compounds may be used as therapies for cancer, such as though not limited to, leukemias, colorectal cancers, pancreatic cancers and lung cancers.

Definitions

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements and components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, and unless otherwise indicated, the term K-ras mediated disorders for which the present methods and compositions may be used include, but are not limited to, leukemias, colorectal cancer, pancreatic cancer and lung cancer.

As used herein, and unless otherwise indicated, the terms "treat," "treating," "treatment" and "therapy" contemplate an action that occurs while a patient is suffering from a K-ras mediated disorder that reduces the severity of one or more symptoms or effects of a K-ras mediated disorder. Where the context allows, the terms "treat," "treating," and "treatment" also refers to actions taken toward ensuring that individuals at increased risk of a K-ras mediated disorder, are able to receive appropriate surgical and/or other medical intervention prior to onset of a K-ras mediated disorder. As used herein, and unless otherwise indicated, the terms "prevent," "preventing," and "prevention" contemplate an action that occurs before a patient begins to suffer from a K-ras mediated disorder, that delays the onset of, and/or inhibits or reduces the severity of a K-ras mediated disorder.

As used herein, and unless otherwise indicated, the terms "manage," "managing," and "management" encompass preventing, delaying, or reducing the severity of a recurrence of a K-ras mediated disorder in a patient who has already suffered from such a disease, disorder or condition. The terms encompass modulating the threshold, development, and/or duration of a K-ras mediated disorder or changing how a patient responds to a K-ras mediated disorder.

As used herein, and unless otherwise specified, a "therapeutically effective amount" of a compound is an amount sufficient to provide any therapeutic benefit in the treatment or management of a K-ras mediated disorder, or to delay or minimize one or more symptoms associated with a K-ras mediated disorder. A therapeutically effective amount of a compound means an amount of the compound, alone or in combination with one or more other therapies and/or therapeutic agents that provide any therapeutic benefit in the treatment or management of a K-ras mediated disorder. The term "therapeutically effective amount" can encompass an amount that alleviates a K-ras mediated disorder, improves or reduces a K-ras mediated disorder, improves overall therapy, or enhances the therapeutic efficacy of another therapeutic agent.

As used herein, and unless otherwise specified, a "prophylactically effective amount" of a compound is an amount sufficient to prevent or delay the onset of a K-ras mediated disorder, or one or more symptoms associated with a K-ras mediated disorder or prevent or delay its recurrence. A prophylactically effective amount of a compound means an amount of the compound, alone or in combination with one or more other treatment and/or prophylactic agent that provides a prophylactic benefit in the prevention of a K-ras mediated disorder. The term "prophylactically effective amount" can encompass an amount that prevents a K-ras mediated disorder, improves overall prophylaxis, or enhances the prophylactic efficacy of another prophylactic agent. The "prophylactically effective amount" can be prescribed prior to, for example, the development of a K-ras mediated disorder.

As used herein, "patient" or "subject" includes mammalian organisms which are capable of suffering from a K-ras mediated disorder as described herein, such as human and veterinary patients as well as non-human mammals, for example, but not limited to, rodents, mice, rats, non-human primates and companion animals such as dogs and cats, etc.

As used herein, the term "about," when used in conjunction with a percentage or other numerical amount, means plus or minus 10% of that percentage or other numerical amount. For example, the term "about 80%," would encompass 80% plus or minus 8%. Further, all references cited herein are incorporated in their entirety.

As used herein the term substantially means at least about 50%, at least about 70%, at least about 80%, or more preferably at least about 90%, and still more preferably at least about 95% of the compound present being in the R-isomeric form.

As used herein the term perturb means to disrupt, inhibit or compromise normal function or operation of a biological process.

As used herein the term trafficking means the active or passive transport of K-Ras proteins from the cytosolic surface of the endoplasmic reticulum to the inner leaflet of the plasma membrane and any active or passive process that then operates to maintain the localization of K-Ras on the inner leaflet of the plasma membrane.

As used herein the term constitutively active refers to a constitutively active protein, wherein the protein's activity is constant and active.

General Principle

In some embodiments provided herein, it is demonstrated that fendiline, fendiline HCL or combinations thereof inhibit normal K-ras association with the plasma membrane resulting in aberrant localization of K-ras protein to the cytosol and other cellular membranes; and inhibit signaling downstream of this protein, and may therefore be used to treat K-ras mediated disorders, such as cancer, specifically, though not limited to, leukemias, colon cancer, pancreatic cancer and lung cancer. In some other embodiments, it was demonstrated that the function of fendiline as a K-ras inhibitor is unrelated to changes in intracellular Ca2+, or blockade of Ca2+ channels.

Figure 10:
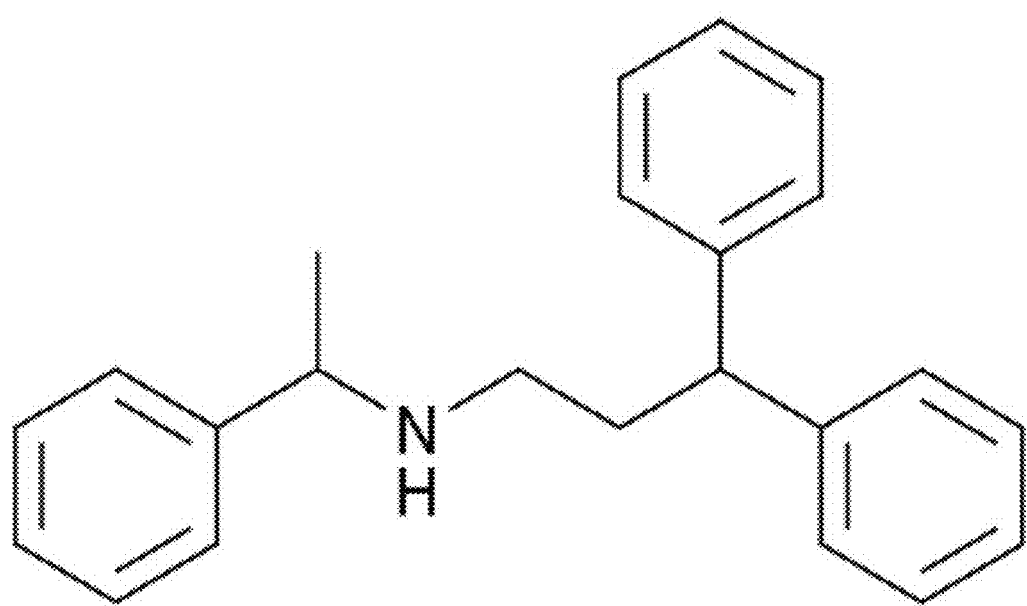
FIG. 10: Illustrates the chemical structure of fendiline (3,3-diphenyl-N-(1-phenylethyl)propan-1-amine) CAS number 13042-18-7.

The chemical formula for fendiline is C23H25N, shown in FIG. 10. The systematic (IUPAC) name for fendiline is 3,3-diphenyl-N-(1-phenylethyl)propan-1-amine (CAS number 13042-18-7, ATC code C08EA01, PubChem CID 3336). The CAS number for fendiline HCl is 13636-18-5 and molecular mass is 351.92337. The typical mode of action of fendiline reported in the prior art is as a selective L-type Ca2+ channel blocker; or a calmodulin antagonist (see for example, Lückhoff A, Bohnert M, Busse R. Effects of the calmodulin antagonists fendiline and calmidazolium on aggregation, secretion of ATP, and internal calcium in washed human platelets. *Naunyn Schmiedebergs Arch Pharmacol.* 1991; 343(1):96-101). However as described herein, fendiline blocks the binding of K-ras protein to plasma membrane in a Ca2+ independent method, thereby herein presenting a new and previously unknown mode of action for Fendiline.

In some embodiments, the concentration of fendiline that inhibits localization of K-ras and thus inhibits signaling that occurs downstream of K-ras occurs at about 0.01 to about 15 microMolar, (for example, but not limited to, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15 microMolar) and the ability of fendiline to disrupt K-ras signaling is unrelated to changes in intracellular Ca2+, or blockade of Ca2+ channels.

In one embodiment Fendiline translocates the K-ras protein; and has little effect on H-ras and N-ras, as demonstrated by using fluorescence microscopy and cellular fractionation. The change in localization of K-ras with the administration of fendiline is observed in one embodiment by fluorescent microscopic imaging; and in a further embodiment in cellular fractionation studies. K-ras becomes associated with the cytoplasm; Golgi, ER; and endosomes when treated with Fendiline.

While not wishing to be limited by any particular theory in one embodiment, the re-localization of K-ras to the endoplasmic reticulum (ER), Golgi, as well as endosomal structures upon treatment with fendiline suggests that in some embodiments fendiline may alter the function of a regulator of K-ras trafficking or membrane association.

In some embodiments of the method of inhibiting K-ras signaling, the compound targets a K-ras polybasic domain, in some further embodiments the compound targets a K-ras polybasic domain, where the polybasic domain is prenylated.

In other embodiments the compound acts to perturb the electrostatic interactions of the polybasic domains and plasma membrane, and in further embodiments of the method the compound acts to perturbs the trafficking of prenylated polybasic domain targeted RAS proteins; and in some further embodiments of the method of inhibiting K-ras signaling, the compound reduces K-ras-plasma membrane nanoclustering; and redistributes K-ras to the endoplasmic reticulum. In other embodiments of the method, blocking increases the binding of a K-ras protein to at least one of: cytosol; endoplasmic reticulum; endosomes; or Golgi apparatus. In a still further embodiment of the method of inhibiting K-ras signaling, the compound inhibits K-ras-dependent RAF-MAPK and PI3K-AKT signaling.

In some embodiments fendiline inhibits the proliferation of endometrial cancer cells that express oncogenic K-ras and the anti-proliferative effect of fendiline is in one embodiment mediated by its ability to inhibit K-ras translocation and signaling, indicating that fendiline can be used as an anti-cancer therapeutic.

Thus, in one embodiment a method of treating a K-ras mediated disorder in a patient in need thereof is provided where the method comprises administering to the patient a therapeutically effective amount of a compound that inhibits K-ras signaling by blocking the association of the K-ras protein with the plasma membrane.

In some embodiments, the compound is fendiline; fendiline HCl or a combination thereof, and in further embodiments of the method, the compound is substantially in R-isomeric form, and in other embodiments the compound may be a racemic mixture.

In a further embodiment of the method of treating a K-ras mediated disorder the compound is used in combination with at least one other chemotherapeutic compound in a combination therapy.

In another embodiment of the method of treating a K-ras mediated disorder, the K-ras mediated disorder is characterized by the presence of a mutant K-ras oncogene. In a further embodiment of the method of treating a K-ras mediated disorder, the K-ras mediated disorder is undesirable or pathologic cell proliferation, and in a still further embodiment the K-ras mediated disorder is cancer, and in another embodiment the cancer is at least one of: leukemia, colorectal cancer, pancreatic cancer, or lung cancer. In some embodiments of the method of treating a K-ras mediated disorder administering to the patient is oral or intravenous, in a further embodiment said administering is oral, and by a controlled release formulation, and in still further embodiments, said patient is human or veterinary. In some embodiments of the method of treating a K-ras mediated disorder the compound inhibits K-ras-dependent RAF-MAPK and PI3K-AKT signaling.

Medicaments, Pharmaceutical Formulations, and Dosages

In some embodiments a medicament comprising a therapeutically effective amount of fendiline or fendiline HCl or a combination thereof is provided, which inhibits K-ras signaling to treat a K-ras mediated disorder in a patient in need of such a treatment. In some embodiments the medicament comprises a further therapeutic compound, and in another embodiment further comprises a pharmaceutical vehicle.

In some embodiments, the therapeutically effective amount of fendiline in plasma is about 0.01 micromolar to about 15 microMolar (for example, but not limited to, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14 or 15 microMolar).

In some embodiments a therapeutically effective dose refers to that amount of the compound sufficient to result in any delay in onset, amelioration, or retardation of disease symptoms, thus in one embodiment, Fendiline can be used alone or in combination with other compounds or excipients, to create a medicament that can be used to treat K-ras mediated disorders.

In further embodiments, toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population), the dose ratio between toxic and therapeutic effects is the therapeutic index, expressed as the ratio $LD_{50}/ED_{50}$. Compositions that exhibit large therapeutic indices are preferred. Data obtained from cell culture assays and animal studies may be used in formulating a range of dosages for use in humans. The dosages of such compositions lie preferably within a range of circulating concentrations that include $ED_{50}$ with little or no toxicity. Plasma levels may be measured, for example, by high performance liquid chromatography.

The appropriate dosage for the therapeutic treatment of K-ras mediated disorders (comprising in some embodiments, leukemia, colorectal cancer, pancreatic cancer and lung cancer) may also be determined using animal studies to determine the maximal tolerable dose, or MTD, of a bioactive agent per kilogram weight of the test subject. Additionally, the compound may be coupled or complexed with a variety of compositions or structures that, for instance, enhance the stability of the compound, or otherwise enhance its pharmacological properties (e.g., increase in vivo half-life, reduce toxicity, etc.).

Such therapeutic agents can be administered by any number of methods known to those of ordinary skill in the art including, but not limited to, inhalation, subcutaneous (sub-q), intravenous (I.V.), intraperitoneal (I.P.), intramuscular (I.M.), or intrathecal injection, or topically applied (transderm, ointments, creams, salves, eye drops, and the like), as described in greater detail below.

The pharmaceutical compositions can comprise formulation materials for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to: amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight polypeptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants ("Remington's Pharmaceutical Sciences", $18^{th}$ Ed. (Gennaro, ed., Mack Publishing Company, Easton, Pa., 1990)).

Additionally, the described compound can be linked to a half-life extending vehicle. Certain exemplary half-life extending vehicles are known in the art, and include, but are not limited to, the Fc domain, polyethylene glycol, and dextran (see, e.g., PCT Patent Application Publication No. WO 99/25044).

Compounds can be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compound can also be formulated as compositions for rectal administration such as suppositories or retention enemas, e.g., containing conventional suppository bases such as cocoa butter or other glycerides.

In addition to the formulations described previously, the compound may also be formulated as a depot preparation. Such long acting formulations may be administered by implantation (for example subcutaneously or intramuscularly) or by intramuscular injection. For example, agents may be formulated with suitable polymeric or hydrophobic materials (for example as an emulsion in an acceptable oil), ion exchange resins, or as sparingly soluble derivatives, for example, as a sparingly soluble salt.

Active compound can be administered by controlled release means or by delivery devices that are well-known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Exemplary sustained release matrices include, but are not limited to, polyesters, hydrogels, polylactides (see, e.g., U.S. Pat. No. 3,773,919 and European Patent Application Publication No. EP 058,481), copolymers of L-glutamic acid and gamma ethyl-L-glutamate (see, e.g., Sidman et al., *Biopolymers* 22:547-556, 1983), poly (2-hydroxyethyl-methacrylate) (see, e.g., Langer et al., *J. Biomed. Mater. Res.* 15:167-277, 1981, and Langer, *Chemtech* 12:98-105, 1982), ethylene vinyl acetate (Langer et al., supra), and poly-D(-)-3-hydroxybutyric acid (European Patent Application Publication No. EP 133,988). Sustained release compounds may include liposomes, which can be prepared by any of several methods known in the art (see, e.g., Eppstein et al., *Proc. Natl. Acad. Sci. USA* 82:3688-3692, 1985, and European Patent Application Publication Nos. EP 036,676, EP 088,046, and EP 143,949). Suitable controlled-release formulations known to those of ordinary skill in the art, including those described herein, can be readily selected for use with the presently disclosed compound. Certain embodiments encompass single unit dosage forms suitable for oral administration such as, but not limited to, tablets, capsules, gelcaps, and caplets that are adapted for controlled-release.

Kits

In one embodiment a kit comprises a single unit dosage form of one or more of the therapeutic agents disclosed. Disclosed kits may further comprise devices that are used to administer the active ingredients. Examples of such devices include, but are not limited to, syringes, drip bags, patches, and inhalers.

Disclosed kits can further comprise pharmaceutically acceptable vehicles that can be used to administer one or more active ingredients. In on embodiment an active ingredient may be provided in a solid form that is reconstituted for parenteral administration, in a further embodiment, the kit may comprise a sealed container of a suitable vehicle in which the active ingredient can be dissolved to form a particulate-free sterile solution that is suitable for parenteral administration. Pharmaceutically acceptable vehicles include, but are not limited to: water for injection USP; aqueous vehicles such as, sodium chloride Injection, Ringer's Injection, dextrose injection, dextrose and sodium chloride injection, and lactated Ringer's Injection; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate. In some embodiments herein described, formulations do not contain any alcohols, co-solvents, oils or proteins.

Methods of Identifying Compounds

The disclosure herein provides in some embodiments a method of identifying a compound that blocks the association of K-ras protein with a plasma membrane; the method comprises: a) incubating MDCK-GFP-Target cells constructs; b) adding a test compound to said cells, and further incubating; c) imaging cells from step b); d) analyzing protein localization in cells of step c; and e) selecting based on step d) compounds that block protein localization compared to a control, wherein said compounds inhibit K-ras signaling. In some embodiments the MDCK-GFP-Target cells are MDCK-GFP-CTK cells, in other embodiment the MDCK-GFP-Target cells are MDCK-GFP-CTH cells.

In accordance with some embodiments described herein, wild type MDCK cells or MDCK cells expressing monomeric green fluorescent protein (mGFP)-tagged C-terminal region of K-ras or H-ras (GFP-CTK and GFP-CTH respectively) were seeded in triplicate in 96 well plates (Matrical) at a density of 30,000 cells/well and incubated for 24 h at 37° C. Compounds were individually added to test cells at a concentration of 4 μg/mL (concentration of DMSO 1%) and incubated for a further 48 h.

Cells were then fixed with 4% paraformaldehyde and stored in PBS at 4° C. until imaged. Plates were imaged using a BD Pathway High-Throughput Bioimager. Images were acquired by a 3×3 montage with 20× objective lens using GFP-confocal mode.

EXAMPLES

The following examples provide further details of various embodiments, described herein. These examples are illustrations of the methods and systems described herein and are non-limiting to the scope of the invention.

Reagents and Techniques Utilized

Prestwick Chemical library and fendiline HCl were purchased from Prestwick Chemicals (Illkirch, France). All other compounds were purchased from Sigma Aldrich (St. Louis, Mo., USA) and were dissolved in DMSO. Cell culture media and Fetal Bovine Serum (FBS) were purchased from HyClone (Thermo Fisher Scientific, HyClone, Logan, Utah, USA). 100× Penicllin/Streptomycin was purchased from Invitrogen (Life Technologies, Grand Island, N.Y., USA). Antibodies against extracellular signal-regulated kinase 2 (ERK2) (sc-521), α-tubulin (sc-5286), N-ras (sc-31) and H-ras (sc-520) were obtained from Santa Cruz Biotechnology (Santa Cruz, Calif.). Anti-c-K-ras (R3400) and anti-β-Actin (A1978) antibodies were from Sigma Aldrich. Anti-Ras (610001) and anti-Raf1 (610152) antibodies were obtained from BD Transduction Laboratories (Lexington, Ky., USA). Anti-phospho-p44/42 mitogen-activated protein kinase (MAPK) (ERK1/2) (Thr202/Tyr204) (#9101), anti-phospho-Akt (pAkt) (Ser473) (#9271) and anti-Akt (#2920) antibodies were from Cell Signaling Technology (Beverly, Mass., USA). Anti-Protein Disulphide Isomerase (PDI) (ab2792) and anti-58K Glgi protein (p58) (ab6284) antibodies were from Abcam (Cambridge, Mass., USA). Mouse anti-GFP antibody for Western immunoblotting was from Sigma (G1546) and rabbit anti-mGFP antibody for immunogold labeling was generated in house. K-ras mouse ON-TARGETplus SMARTpool, ON-TARGETplus Non-targeting Pool, DharmaFECT 1 siRNA Transfection Reagent, and 5× siRNA Buffer were purchased from Dharmacon (Lafayette, Colo., USA). Recombinant MEK1 (14-420) and ERK2 (14-198) were purchased from Millipore (Billerica, Mass., USA).

Cell lines. BxPC3, HPAC, MOH, MiaPaCa-2, MPanc96 cells, Hec-50 cells; KLE, ESS1, Ishikawa, Hec-1a and HEC-1b were provided by MD Anderson Cancer Center, Houston, Tex. All other cell lines were purchased from the American Type Culture Collection (Manassas, Va.). Madin-Darby canine kidney (MDCK) epithelial cells and baby hamster kidney (BHK) cells were grown in Dulbecco's modified Eagle's medium (DMEM)-high-glucose medium supplemented with sodium pyruvate and 10% FBS or supplemented bovine calf serum, respectively. KLE and Hec-50 cells were maintained in DMEM-F-12 medium supplemented with 10% FBS. Hec-1a and Hec-1b cells were grown in McCoy's 5a medium supplemented with 10% FBS. Ishikawa cells were maintained in minimal essential medium (MEM) supplemented with sodium pyruvate, non-essential amino acids, and 5% FBS, and ESS-1 cells were grown in RPMI 1640 medium supplemented with 20% FBS. MPanc96 and CaCO-2 cells were grown in DMEM supplemented with 10% FBS, MiaPaCa-2 cells in DMEM supplemented with 10% FBS and 2.5% horse serum, and SK-CO-1 cells in Eagle's MEM supplemented with 10% FBS. SW116 and SW948 cells were grown in Leibovitz's L15 medium with 10% FBS. All other cell lines were grown in RPMI 1640 supplemented with 10% FBS. SW116 and SW948 cells were grown at 37° C. without CO2. All other cell lines were grown at 37° C. with 5% CO2. BHK cells were transfected using Lipofectamine (Invitrogen) according to the manufacturer's instructions. Where necessary, the cells were serum starved for 2.5 h prior to harvest.

Cells Used in Screening Assays:

In accordance with embodiments herein described, MDCK cells that stably express GFP-CTK (K-ras) or GFP-CTH (H-ras) were used in the screening assay. GFP-CTK constructs contained the complete carboxy-terminal hypervariable region of K-ras (amino acids 166-188) cloned onto the carboxy terminus of GFP. GFP-CTH constructs contained the complete carboxy-terminal hypervariable region of H-ras (amino acids 166-189) cloned onto the carboxy terminus of monomeric GFP.

In T75 flasks, MDCK, MDCK-GFP-CTK, and MDCK-GFP-CTH cells were grown to confluency in DMEM high glucose medium containing 10% FBS/Na pyruvate. At confluency, the cells were washed twice with D-PBS (without $Ca^{2+}$) (10 mL), and 2 mL of 0.25% Trypsin-EDTA was added. Flasks were incubated at 37° C. for 5 minutes, at which time the cells had risen off the flasks and 8 mL of medium was added, the cells were resuspended and then transferred to a 50 mL tube. Cells were pelleted using centrifugation, the supernatant decanted, and the cells were resuspended in 20 mL of medium. In order to free clumped cells, the cells were passed through a 22 G needle, 5 times. Cells were then enumerated using a hemocytometer. Then a 30 mL cell suspension was prepared at a concentration of $3 \times 10^5$ cells/mL in DMEM medium containing 10% FBS/Na pyruvate with 300 uL of 100× Pen/Strep added.

One hundred (100) uL of cell suspension (containing approximately 30,000 cells) was distributed to the wells of three 96 well metrical plates (three plates were prepared for each cell type). To allow for even distribution of the cells in each well, the plates sat at room temperature for about 10 minutes in the cell culture hood. The plates were then transferred to an incubator for storage for 24 hours. To wash the cells, the media in the wells was removed and replaced with D-PBS (containing Ca2+) (100 uL per well), and then this wash was removed. Fresh DMEM high glucose medium containing 10% FBS/Na pyruvate/1× PenStrep (100 uL) was added to each well, as was 1 uL of test compound (applied at a concentration of 4 µg/mL) in DMSO to appropriate wells. The plates were incubated for 48 hours at 37° C. To wash the cells the media from the cells was removed and replaced with D-PBS (containing Ca2+) (100 uL), twice and then the wash was removed and the cells were fixed by the addition of 100 uL of 4% paraformaldehyde and incubated at RT for 30 min (in dark). Fixed cells were stored in PBS at 4° C. until they could be imaged.

Plates containing fixed cells were warmed to room temperature and the cells were imaged using BD Pathway High-Throughput Bioimager. Images were acquired in Tiff format as 3×3 montage with 20× objective lens using GFP-confocal mode. Images were analyzed by two independent individuals using Adobe Photoshop and observations recorded in Excel spread sheets. Compounds that affected K-ras and/or H-ras localization were chosen for a secondary or confirmatory screen using the same protocol, Fluorescence Microscopy:

Cells were further analyzed using fluorescence microscopy, where cells were grown on coverslips, treated with 1% vehicle (DMSO) or varying concentrations of selected compounds for 48 h, and fixed with 4% paraformaldehyde. The coverslips were mounted in Mowiol® and visualized by confocal microscopy (Nikon A1) using a 60× objective. The cells were immuno-staining, where cells were fixed, permeabilized in 0.1% Triton in PBS for 30 min, and blocked with 0.2% bovine serum albumin and 0.2% fish skin gelatin in PBS for 30 min. Primary and secondary antibodies were incubated for 1 h each, and then coverslips were mounted in Mowiol®.

K-Ras Knockdown:

BHK cells expressing GFP-tagged H-rasG12V were transfected with the ON-Target K-ras specific siRNA pool or non-targeting control siRNA pool (Dharmacon, Inc., Lafayette, Colo., USA) according to manufacturer's protocol. At 24 h post-transfection, the cells were treated with vehicle or Fendiline HCl; 48 h later (72 h total knockdown time) the cells were lysed for Western blot analysis.

Western Blotting:

Preparation of whole-cell lysates: cells were lysed in Buffer B (50 mM Tris [pH 7.5], 75 mM NaCl, 25 mM NaF, 5 mM $MgCl_2$, 5 mM EGTA, 1 mM dithiothreitol, 100 µM $NaVO_4$, 1% Nonidet P-40 plus protease inhibitors). Cellular fractionation: cells were incubated in Buffer A (10 mm Tris-HCl, pH 7.5, 25 mm NaF, 5 mm $MgCl_2$, 1 mm EGTA, 1 mm dithiothreitol, 100 µm NaVO4 plus protease inhibitors) for 30 minutes on ice and lysed by passing through a 27 G needle 30 times. The post nuclear supernatant was centrifuged at 100,000 g for 30 minutes and the membrane pellet was resuspended in Buffer A containing 1% Triton X-100.

SDS-PAGE and Western blotting with the specified antibody were performed using 20 µg of each whole cell lysate/P100 fraction and volumes of S100 equal to that of the corresponding P100. Signal was detected by enhanced chemiluminescence (SuperSignal; Pierce, Thermo Fisher Scientific, Rockford, Ill.) and imaged by FluorChemQ (Alpha Inotech, San Leandro, Calif., USA). Quantification of intensities was performed using FluorChemQ software.

Immuno-Electron Microscopy (EM) and Spatial Analysis:

Immuno-EM and spatial analysis were conducted exactly as described previously (Hancock, J. F., and Prior, I. A. (2005). Electron microscopic imaging of Ras signaling domains. *Methods* 37, 165-172; Prior, I. A., Muncke, C., Parton, R. G., and Hancock, J. F. (2003). Direct visualization of Ras proteins in spatially distinct cell surface microdomains. *J Cell Biol* 160, 165-170). Plasma membrane sheets were prepared, fixed, and labeled with affinity-purified anti-GFP antibody coupled directly to 5-nm gold. Digital images of the immunogold-labeled plasma membrane sheets were taken in a transmission electron microscope. Intact 1-$\mu m^2$ areas of the plasma membrane sheet were identified using ImageJ, and the x-y coordinates of the gold particles were determined. Ripley's K function (Ripley, B. D. (1977). Modeling spatial patterns. *J. R. Statist. Soc. B* 39, 172-192) was calculated using the x-y coordinates and then standardized on the 99% confidence interval (CI) for a random pattern ((Hancock, et al., 2005, ibid; Prior, et al., 2003, ibid); Diggle, P. J., J. Mateu, and H. E. Clough. (2000). A comparison between parametric and non-parametric approaches to the analysis of replicated spatial point patterns. *Adv. Appl. Probab.* 32, 331-343). Bootstrap tests to examine differences between replicated point patterns were constructed exactly as described previously, and statistical significance was evaluated against 1,000 bootstrap samples (Diggle, et al., 2000, ibid; Plowman, S. J., Muncke, C., Parton, R. G., and Hancock, J. F. (2005). H-ras, K-ras, and inner plasma membrane raft proteins operate in nanoclusters with differential dependence on the actin cytoskeleton. *Proc Natl Acad Sci USA* 102, 15500-15505).

Raf Kinase Assay:

Membrane (P100) fractions were prepared from BHK or MDCK cells were dissolved in Buffer A containing 1% TritonX100. Solubilized P100 fractions were incubated with combinations of recombinant MEK and ERK in the presence of $Mg^{2+}$-ATP (40 mM and 0.5 mM, respectively) After 30 min at 30° C. with vigorous shaking, the pMEK and ppERK levels were determined by quantitative Western blotting.

Proliferation Assay:

BxPC-3 (4×103 cells per well), MiaPaCa-2 (2×103), MOH (1.5×103), HPAC (7×103), MPanc96 (2×103), KLE (1×104), Hec-1A (5×103), Hec-1B (5×103), Ishikawa (5×103), ESS-1 (5×103), NCI 1975 (6×103), NCI H1299 (3×103), NCI H23 (1×104), NCI H522 (5×103), SNU-C1 (4×103), NCI H508 (4×103), CaCO-2 (5×103), SK-CO-1 (3×103), SW948 (4×103), and SW1116 (6×103) cells were seeded in 96-well plates. After 24 h, fresh growth medium supplemented with 1% vehicle (DMSO), various concentrations of fendiline, or U0126 was added and cells were grown for 48 h or 72 h. Cell numbers were quantified using the CellTiter 96 AQueous One Solution cell proliferation assay (MTS) (Promega), according to the manufacturer's protocol.

Statistical Analysis:

Prism (Version 5.0c, GraphPad Software) was used for statistical analysis,

Example 1

Assay to Identify Compounds that Inhibit K-ras Localization to the Plasma Membrane In accordance with embodiments herein described, screens were used to search for chemicals that inhibit the plasma localization of Ras proteins. MDCK cell lines were established which stably expressed mGFP targeted to the plasma membrane by the minimal C-terminal hypervariable region (HVR) of K-ras (GFP-CTK) or H-ras (GFP-CTH), and MDCK cell lines stably expressing full-length oncogenic mutant GFP-K-rasG12V or GFP-HrasG12V.

For primary screening the cell lines GFP-CTK and GFP-CTH were used. MDCK cells dispensed in 96 well plates were grown in the presence of assayed compounds for 48 h before fixation and imaging. This time frame was chosen to allow trafficking of newly synthesized GFP-Ras proteins and turnover of GFP-Ras protein that was already present when treatment was started. Positive controls cells were treated with 10 µM FTI-276, a farnesyl transferase inhibitor that causes cytoplasmic localization of GFP-CTH but not GFP-CTK and 250 ng/mL UCN-01, a natural product that causes mislocalization of both GFP-CTK and GFP-CTH (FIG. 1). Confocal Images were scored for loss of plasma membrane localization and intracellular accumulation GFP. This assay scores for loss of plasma membrane localization (and/or increased cytoplasmic expression) of GFP-CTK but not GFP-CTH, compared to that observed with vehicle-treated control.

This screen was carried out in order to identify compounds that target K-ras, thus the preferred compounds mislocalized GFP-CTK while having minimal or no effect on GFP-CTH, compared to the vehicle-treated respective control.

Using this screening technique, one compound from the Prestwick Library (1120 compounds), fendiline HCl, specifically affected localization of GFP-CTK but not GFP-CTH at the concentration used for screening (4 ug/ml). Subsequent studies with fendiline HCl using MDCK and BHK cells expressing GFP-tagged full length constitutively active Ras (G12V) proteins confirmed that the compound was a more potent inhibitor of plasma membrane localization of the K isoform as compared to H (FIG. 2A) and N. Immunofluorescence studies in BHK cells using PDI and p58 as ER and Golgi markers, respectively, showed that upon treatment with fendiline HCl, GFP-K-rasG12V partially mislocalizes to the ER and golgi (FIG. 2B).

Example 2

Ca2+ Independent Re-Localization of K-ras by Fendiline HCl

Figure 2:
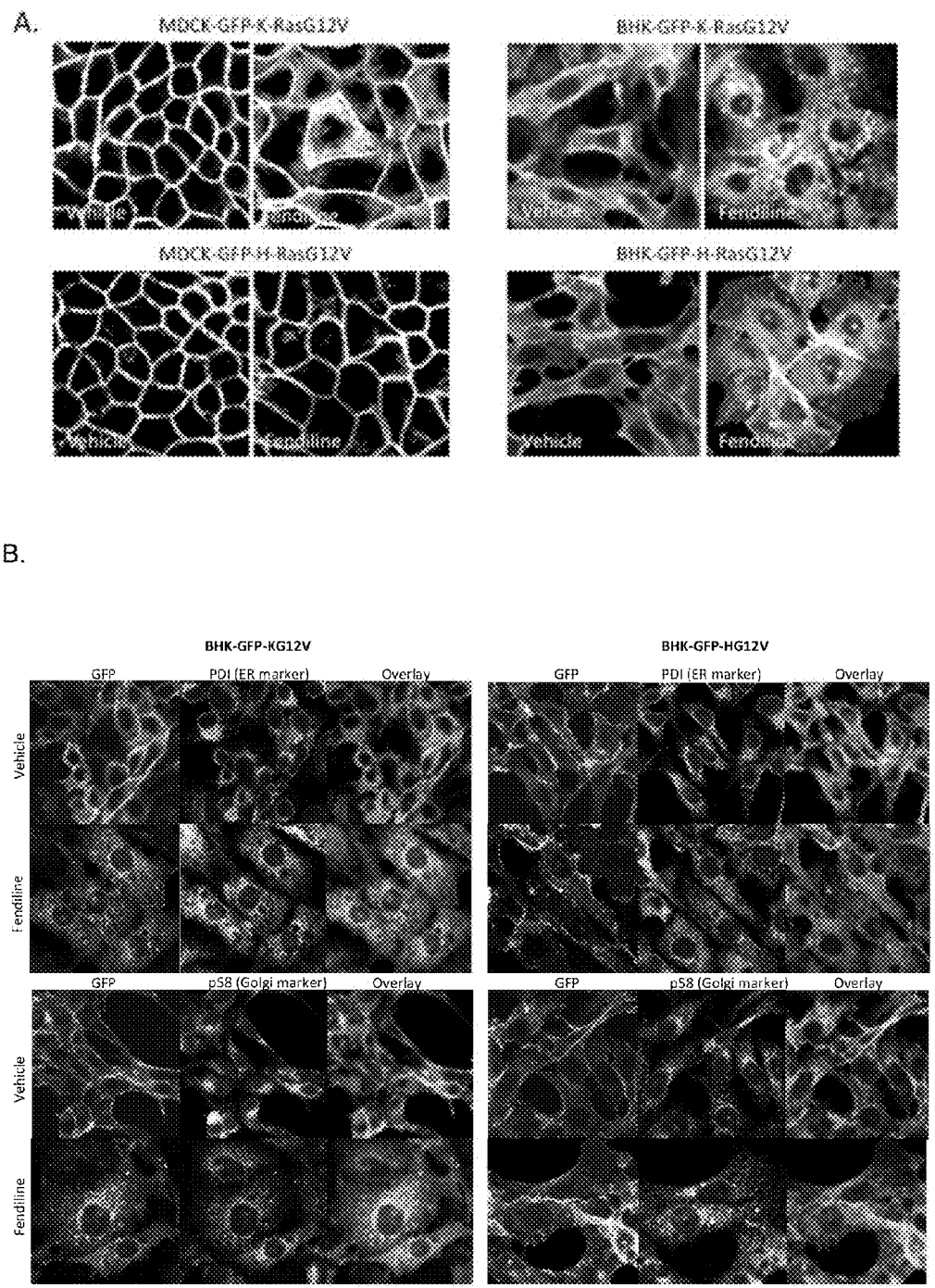
FIG. 2: Illustrates that fendiline HCl mislocalizes GFP-K-rasG12V but not GFP-H-rasG12V: (A) MDCK or BHK [Baby Hamster Kidney] cells expressing GFP-K-rasG12V or GFP-H-rasG12V were grown on cover slips, treated with vehicle or fendiline HCl (4 µg/mL for MDCK and 6 µg/mL for BHK) for 48 h and fixed with paraformaldehyde. Cells were imaged using a confocal microscope. (B) BHK cells expressing GFP-K-rasG12V or GFP-H-rasG12V (green) were treated with vehicle or fendiline HCl (6 µg/mL) for 48 h. Following treatment, cells were fixed and immuno-labeled with antibodies against PDI (ER marker-red) or p58 (golgi marker-red). Colocalization between GFP and the respective marker protein is shown in yellow. Shown are representative images from 3 independent experiments wherein experimentation was performed in accordance with principles described herein.
Figure 3A:
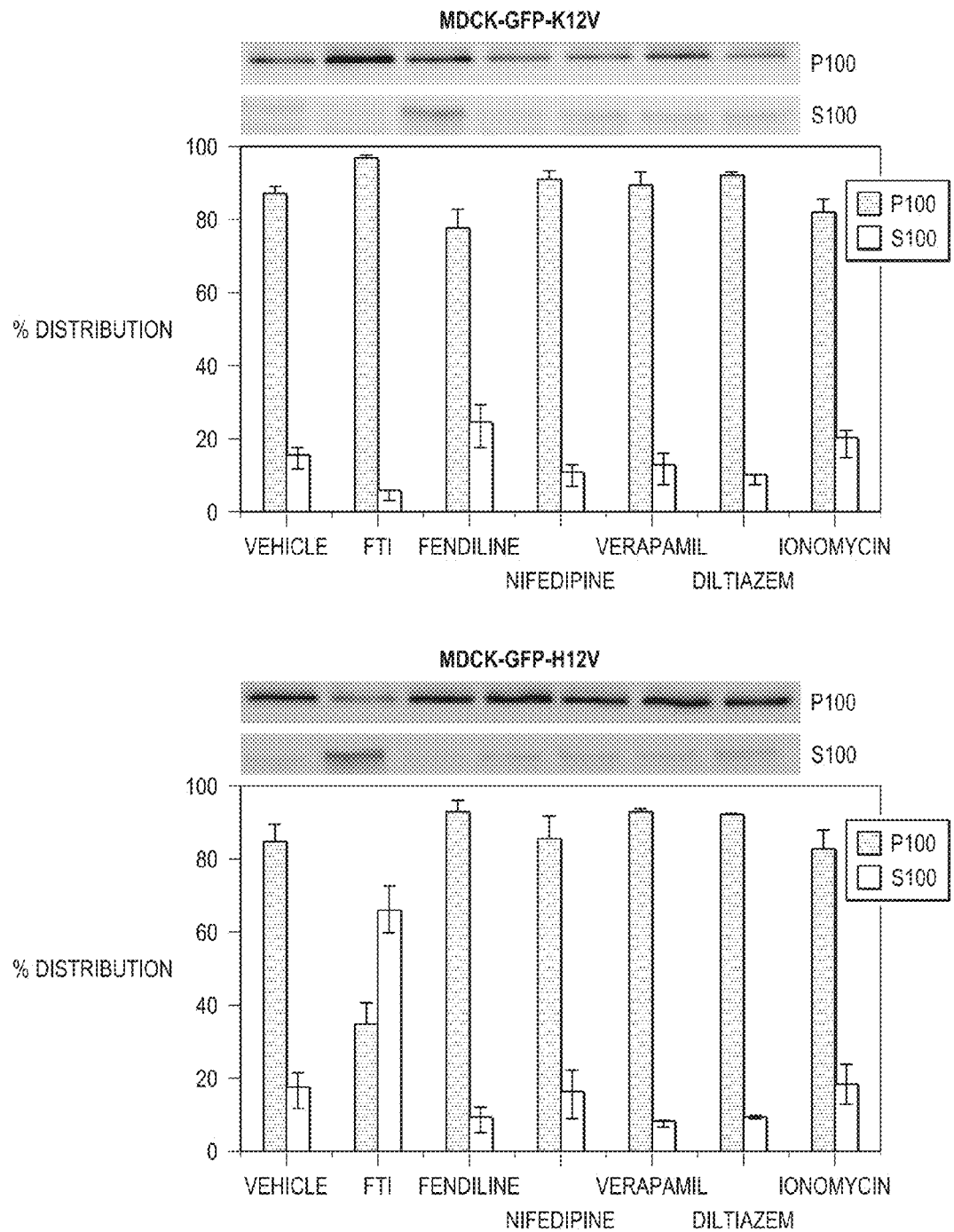
FIG. 3: Illustrates that fendiline HCl increases soluble fraction of GFP-K-rasG12V but not GFP-H-rasG12V: (A) MDCK or (B) BHK cells expressing GFP-K-rasG12V or GFP-H-rasG12V were treated with vehicle, FTI-276 (10 µM), fendiline HCl (4 µg/mL for MDCK and 6 µg/mL for BHK), nifedipine (10 µM), verapamil (10 µM), diltiazem (10 µM), or ionomycin (1 µM) for 48 hours. Following treatment, membrane (P100) and soluble (S100) protein fractions were prepared and analyzed by quantitative Western blotting. Shown are representative Western blots (showing GFP-Ras) of membrane and soluble protein fractions from 3 independent experiments. Data is shown as mean±SEM from 4 independent experiments Statistical significance was calculated using Student's T-Test (*=p<0.05), wherein experimentation was performed in accordance with principles described herein.
Figure 3B:
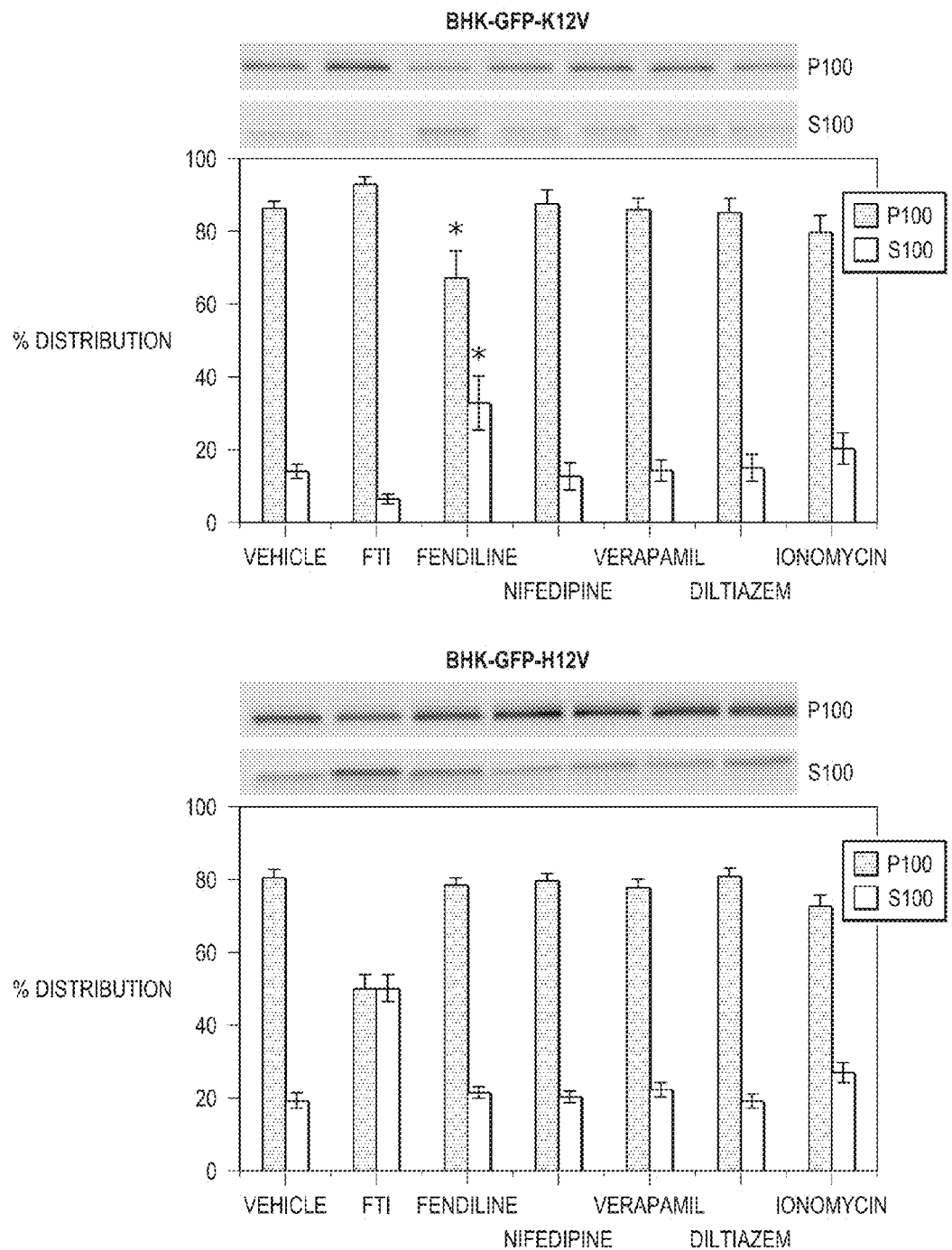

In accordance with one embodiment, herein described, cellular fractionation studies confirmed that treatment with fendiline HCl increases the soluble fraction of GFP-K-rasG12V but does not alter the localization of GFP-H-rasG12V compared to the vehicle-treated control samples in both MDCK (FIG. 2A) and BHK cells (FIG. 2B). Further, since fendiline HCl is a known $Ca^{2+}$ channel blocker, the effect of nifedipine, verapamil and diltiazem, which represent three different classes of $Ca^{2+}$ channel blockers, on the localization of Ras proteins was investigated (FIG. 3). None of the other $Ca^{2+}$ channel blockers altered the localization of GFP-K-rasG12V. Considering that fendiline HCl also has been shown to increase intracellular $Ca^{2+}$ in human oral cancer cells, PC3 prostate cancer cells and MDCK cells, the effect of intracellular $Ca^{2+}$ elevating agent ionomycin on GFP-K-rasG12V localization was examined. Ionomycin did not significantly alter the localization of Ras proteins, indicating that the effect of fendiline is unique and is independent of intracellular $Ca^{2+}$.

Example 3

Fendiline HCl Reduces Membrane Association and Clustering of K-ras

Figure 4A:
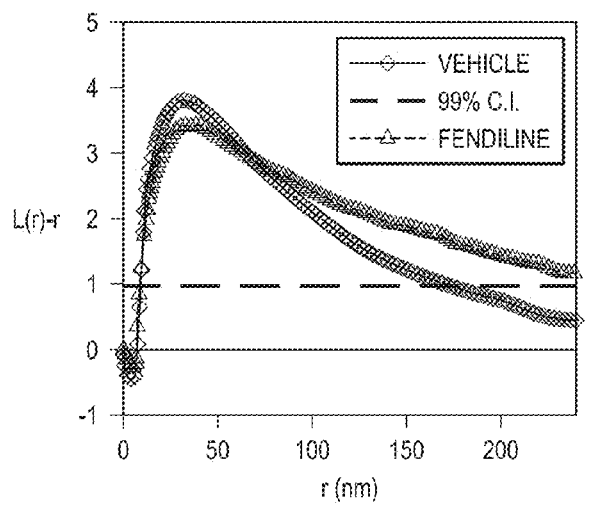
FIG. 4: Illustrates that fendiline HCl alters plasma membrane association and nanoclustering of K-ras: Plasma membrane sheets were generated from cells expressing GFP-K-rasG12V or GFP-H-rasG12V. Cells were treated with vehicle or fendiline HCl (6 µg/mL) for 48 h. Plasma membrane sheets were labeled with anti-GFP antibody conjugated to 4.5 nm gold. The plasma membrane sheets were imaged in an electron microscope and the spatial distribution of the gold labeling was analyzed using Ripley's K-function. Maximum L(r)-r values above the 99% confidence interval (C.I.) for complete spatial randomness (CSR) indicate clustering at that value of r. Univariate K-functions are weighted means (n≥8) standardized on the 99% C.I. for a random pattern. Significant differences from the control pattern for fendiline treated cells were assessed using bootstrap tests, wherein experimentation was performed in accordance with principles described herein.
Figure 4B:
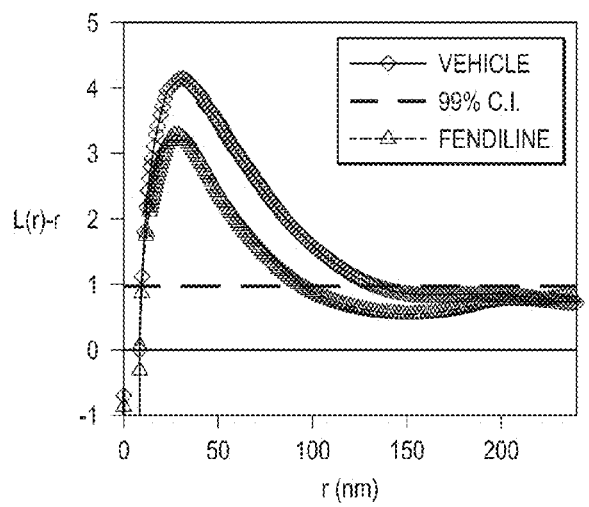
Figure 4C:
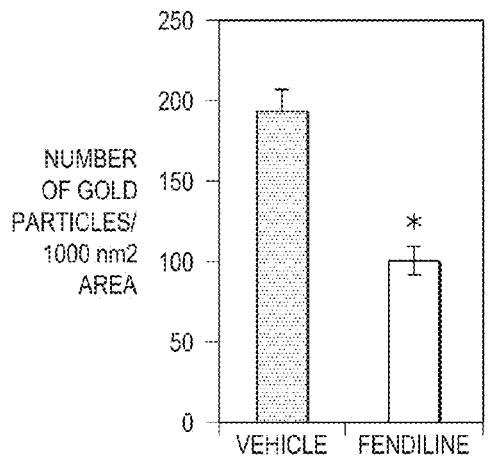
Figure 4D:
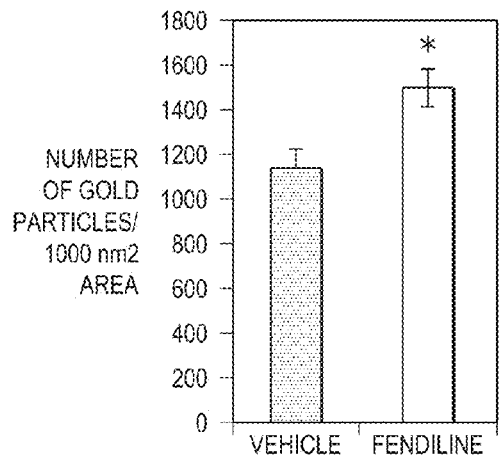

In accordance one embodiment, herein described, Fendiline HCl alters the nanoclustering of Ras proteins. Intact plasma membrane sheets from BHK cells expressing mGFP-tagged K-rasG12V or H-rasG12V, treated with vehicle or fendiline HCl were labeled with anti-mGFP conjugated to 4.5 nm gold. Spatial analysis of the immunogold point pattern visualized by EM revealed that fendiline HCl reduced clustering of both K- and H-rasG12V proteins (FIGS. 4A and B, respectively). In addition, results of the EM analysis further confirmed that fendiline HCl reduces the plasma membrane associated K-rasG12V (FIG. 4C) but slightly increases membrane association of H-rasG12V (FIG. 4D).

Example 4

Fendiline HCl Abrogates Signaling Downstream of K-ras

Figure 5A:
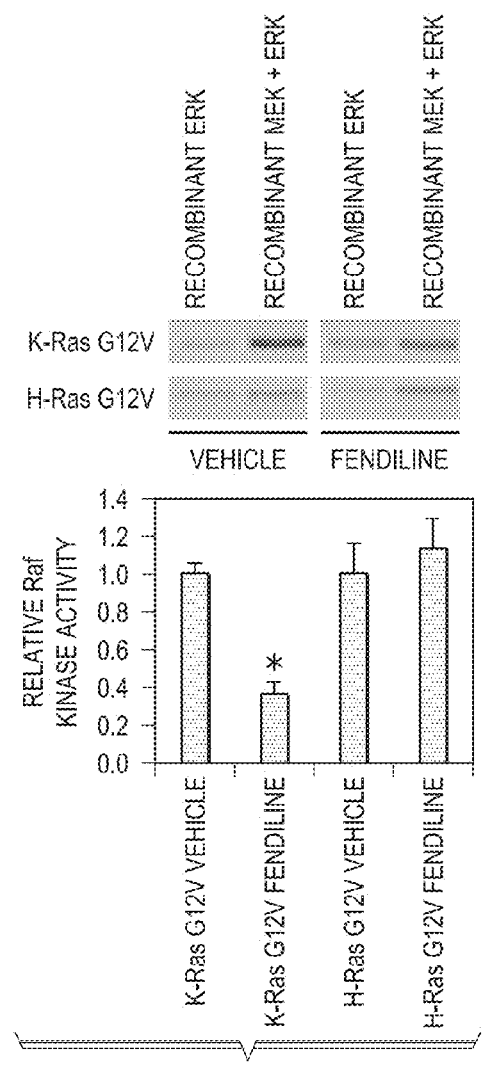
FIG. 5: Illustrates that fendiline HCl inhibits Raf kinase activity and signaling downstream of oncogenic K-ras: BHK cells stably expressing K-rasG12V were treated with vehicle or fendiline HCl (6 µg/mL) for 48 h. (A) Raf kinase activity in membrane fractions prepared from the cells was measured in a coupled EMK/ERK kinase assay. Data is shown as mean±SEM from 3 independent experiments. (B) ppMEK and ppERK in soluble protein fraction and pAkt levels in membrane protein fraction were measured by quantitative Western blotting. Actin and Akt were used as loading controls for soluble and membrane fractions, respectively. A representative blots are shown. Data is shown as mean±SEM from 3-4 independent experiments. Statistical significance was calculated using one way ANOVA and Student's T-test. (*=p<0.05), wherein experimentation was performed in accordance with principles described herein.
Figure 5B:
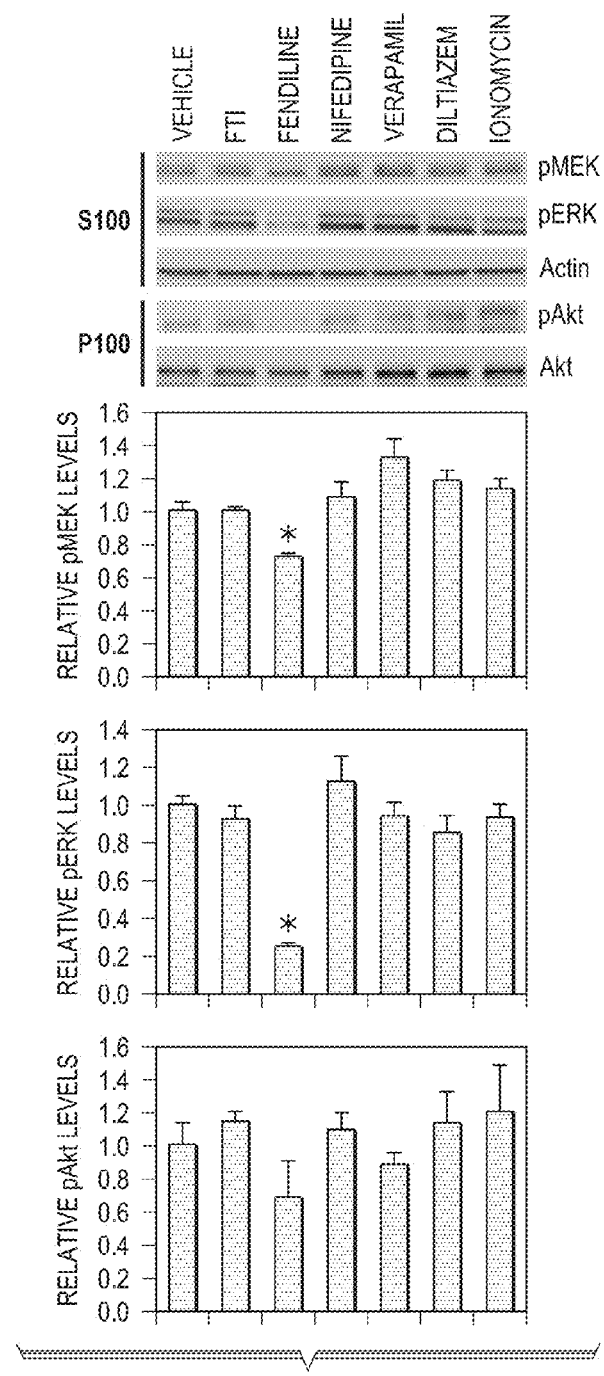

Ras has to be plasma membrane localized for the downstream signaling to occur. Therefore, to demonstrate that fendiline HCl inhibits signaling downstream of activated Ras, the activation of the Raf-MEK-ERK and PI3K-Akt signaling axes were determined In accordance one embodiment, herein described, by measuring Raf kinase activity, pMEK, pERK and pAkt levels by Western blot (FIG. 5). Comparison of Raf kinase activity (as determined by the levels of phosphorylation of recombinant ERK substrate) demonstrated that treatment of cells with fendiline HCl reduces the amount of active Raf by approximately 60% compared to the vehicle-treated control (FIG. 5A). Accordingly, fendiline HCl also significantly reduces the cellular levels of pMEK and pERK compared to vehicle-treated controls and also decreases the pAkt levels, although not statistically significant (FIG. 5B). None of the other $Ca^{2+}$ channel blockers tested or ionomycin had any effect on Ras signaling, confirming the earlier finding that the effect of fendiline HCl on Ras localization and signaling is independent of its ability to alter intracellular $Ca^{2+}$.

Figure 6:
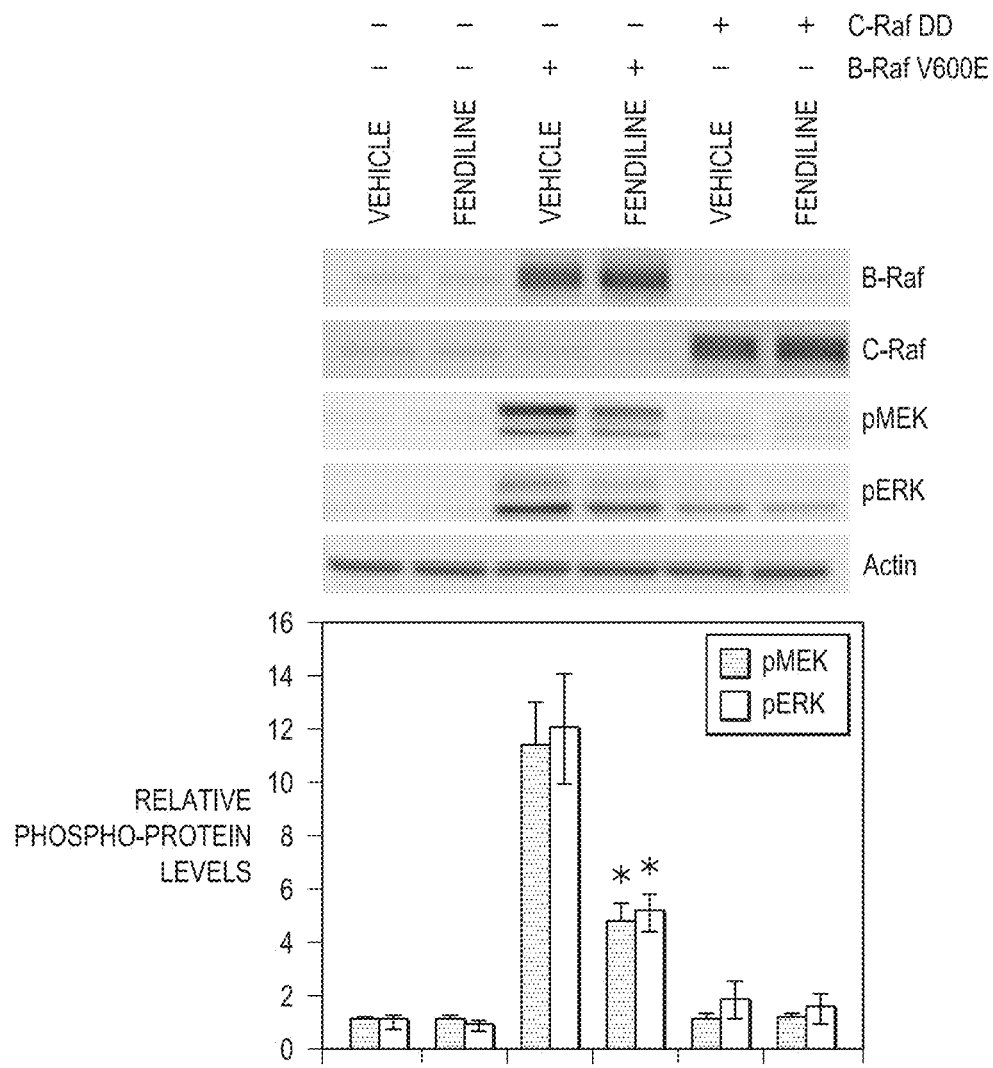
FIG. 6: Illustrates that fendiline HCl inhibition occurs at the level of Ras: Whole cell lysates from serum starved BHK cells expressing vector control, FLAG-C-Raf-DD-CAAX or Myc-B-Raf V600E treated with vehicle or fendiline HCl (6 µg/mL) for 48 h were analyzed by quantitative Western blotting. Representative Western blots of c-Raf, pMEK, pERK and Actin (loading control) are shown. Data is shown as mean±SEM from 3-4 independent experiments. Statistical significance was calculated using one way ANOVA and Student's T-test. (*=p<0.05), wherein experimentation was performed in accordance with principles described herein.

To verify that the inhibition of signaling was not due to a non-specific effect of fendiline HCl on the effectors downstream of Ras, its effect on signaling in cells expressing constitutively active CRaf (Flag-Raf-YY340/341DD), or the more clinically relevant constitutively active BRaf mutant (myc-BRaf-V600E) was also evaluated. Fendiline HCl had no effect on signaling downstream of constitutively active CRaf but inhibited signaling downstream of constitutively active BRaf (FIG. 6), indicating that its inhibition is specific to a signaling molecule upstream of Raf, which is Ras.

Example 6

Fendiline HCl Specifically Inhibits Signaling of K-ras

Figure 7A:
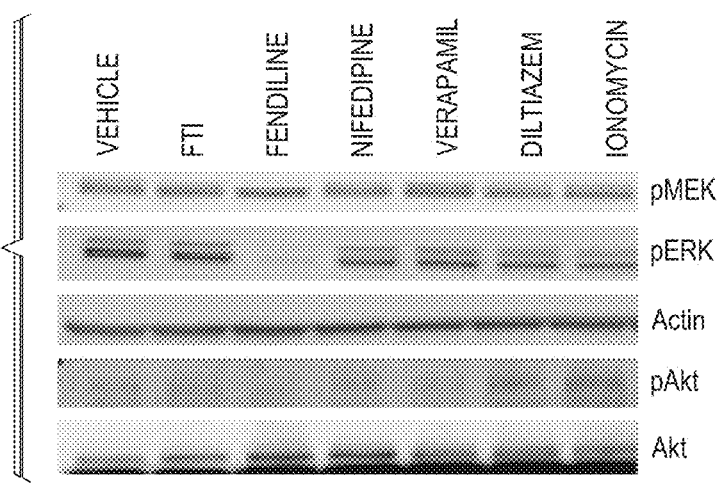
FIG. 7: Illustrates that H-rasG12V signals through endogenous K-ras: BHK cells stably expressing H-rasG12V were treated with vehicle or fendiline HCl (6 µg/mL) for 48 h. (A) ppMEK and ppERK in soluble protein fraction and pAkt levels in membrane protein fraction were measured by quantitative Western blotting. A representative blots are shown. (B) BHK cells stably expressing H-rasG12V were transfected with K-ras siRNA encoding plasmid. 24 h after transfection, cells were treated with vehicle or fendiline HCl (6 µg/mL) for a further 48 h. Whole cell lysates were prepared from serum starved cells and analyzed by quantitative Western blotting. Representative Western blots are shown. Data is shown as mean±SEM from 6 independent experiments. Statistical significance was calculated using Student's T-test. (*=p<0.05), and experimentation was performed in accordance with principles described herein.
Figure 7B:
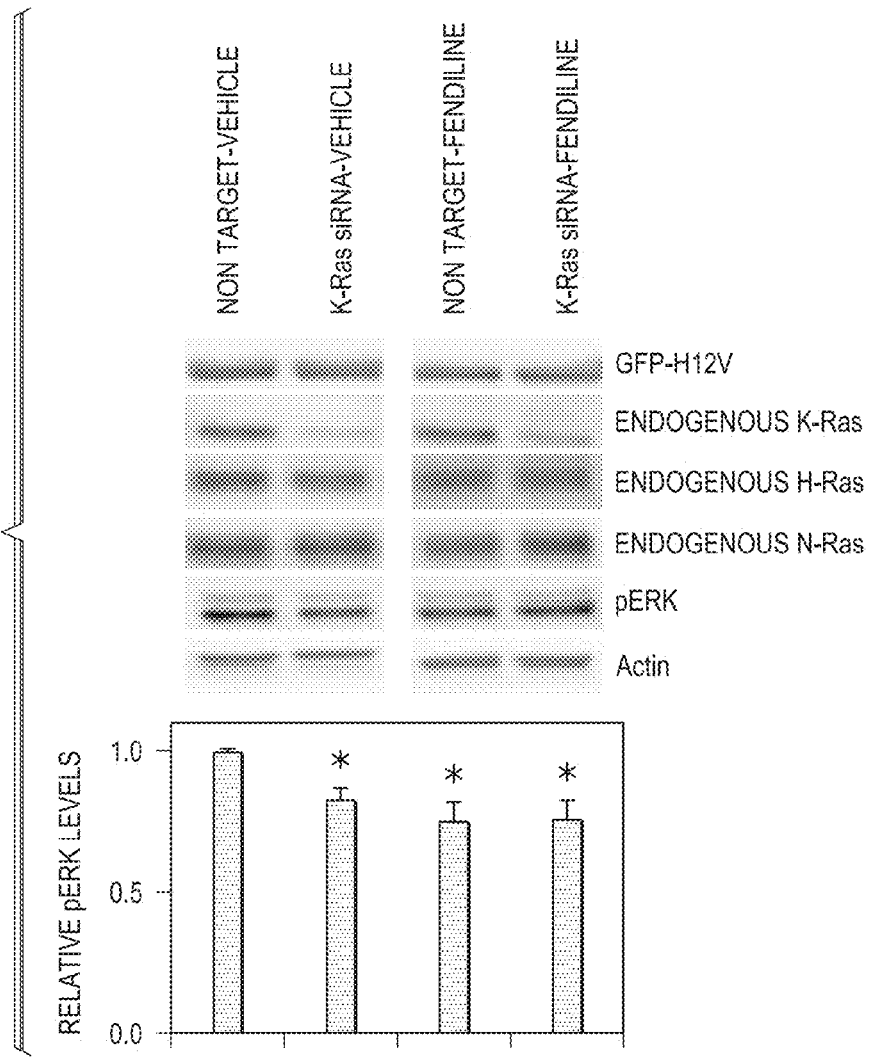

To further demonstrate that the effect of fendiline HCl on signaling is Ras isoform specific, the effect on signaling in cells expressing constitutively active H- or N-Ras was determined. Fendiline HCl decreased the pMEK, pERK and pAkt levels in MDCK and BHK cells expressing oncogenic mutant H-RasG12V, to the similar extent as in the K-rasG12V expressing cells (FIG. 7A) but had no effect on signaling downstream of oncogenic N-ras (data not shown). To demonstrate that inhibition of oncogenic H-ras signaling by fendiline HCl occurs via its effect on endogenous K-ras, the expression of endogenous K-ras was knocked down using siRNA and quantified the pERK levels in the absence or presence of treatment with fendiline HCl. Knock down of endogenous K-ras in BHK cells expressing constitutively active H-ras mimicked the effect of fendiline HCl on pERK levels and treatment with fendiline HCl did not further reduce pERK levels in cells in which endogenous K-ras is knocked down as evidenced by the western blot analysis of FIG. 7B.

Example 7

Figure 8A:
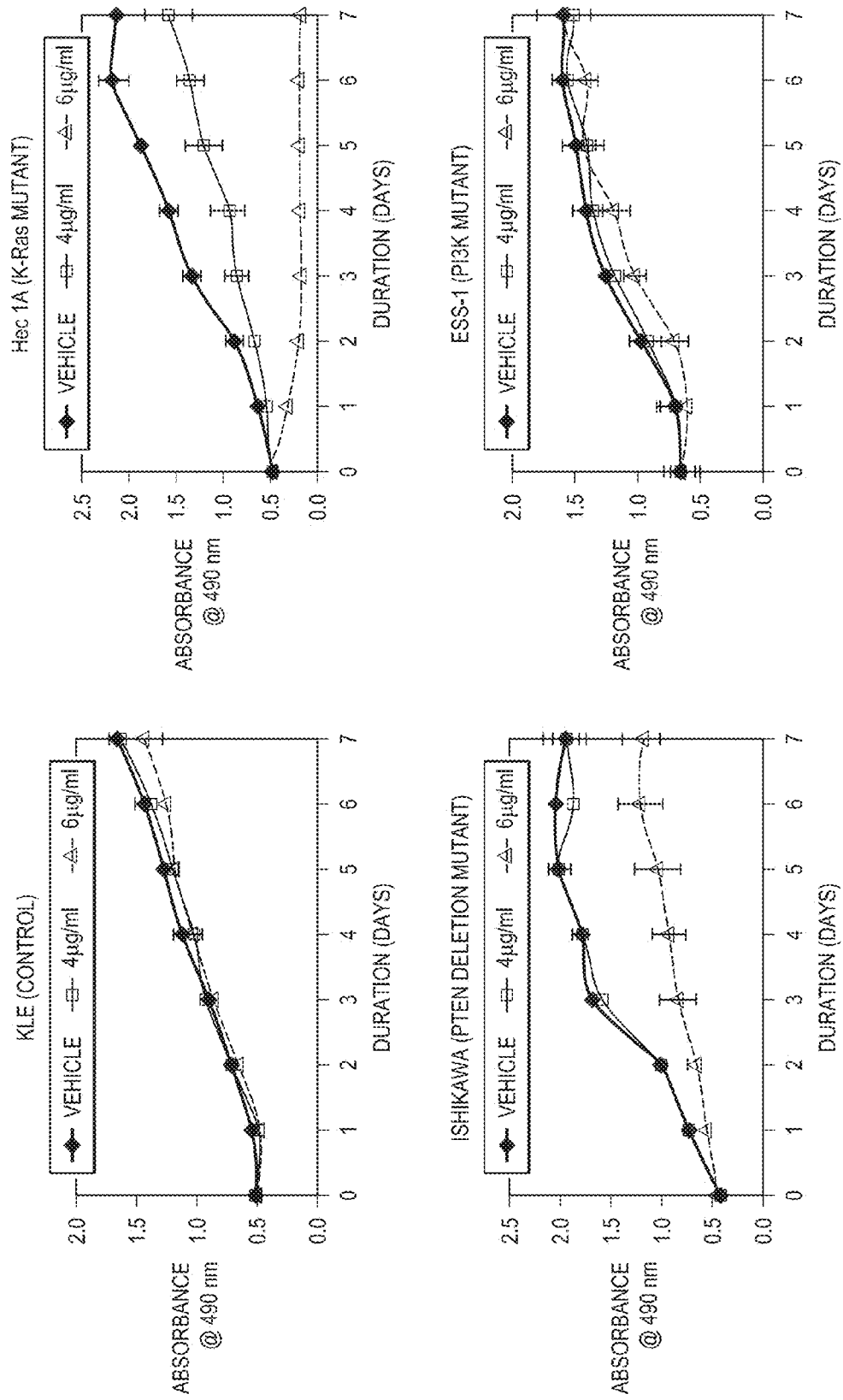
FIG. 8: Illustrates that fendiline selectively inhibits proliferation of tumor cell lines expressing oncogenic mutant K-Ras. (A) A panel of wild-type (WT) or oncogenic mutant (Mut) K-Ras-expressing tumor cells were seeded in 96-well plates and treated for 72 h with vehicle (DMSO) or various concentrations of fendiline. The number of viable cells was quantified (absorbance at 490 nm) using the CellTiter 96 AQueous One Solution cell proliferation assay kit (Promega). The graphs show relative mean numbers of viable cells±SEMs from 3 independent experiments. Cell lines expressing oncogenic mutant K-Ras are shown in red, and cell lines that express wild-type K-Ras are shown in black. NCI H1299 cells (shown in blue) express wild-type K-Ras but mutant N-Ras. CaCO-2 cells (shown in green) overexpress wild-type K-Ras. (B) K-Ras levels in whole-cell lysates of SNU-C1, CaCO-2, and SK-CO-1 cells were quantified by Western blotting. The graphs show means±SEMs for 3 isolates of each cell line (indicated as 1, 2, and 3). K-Ras expression was normalized to the SNU-C1 sample.
Figure 8B:
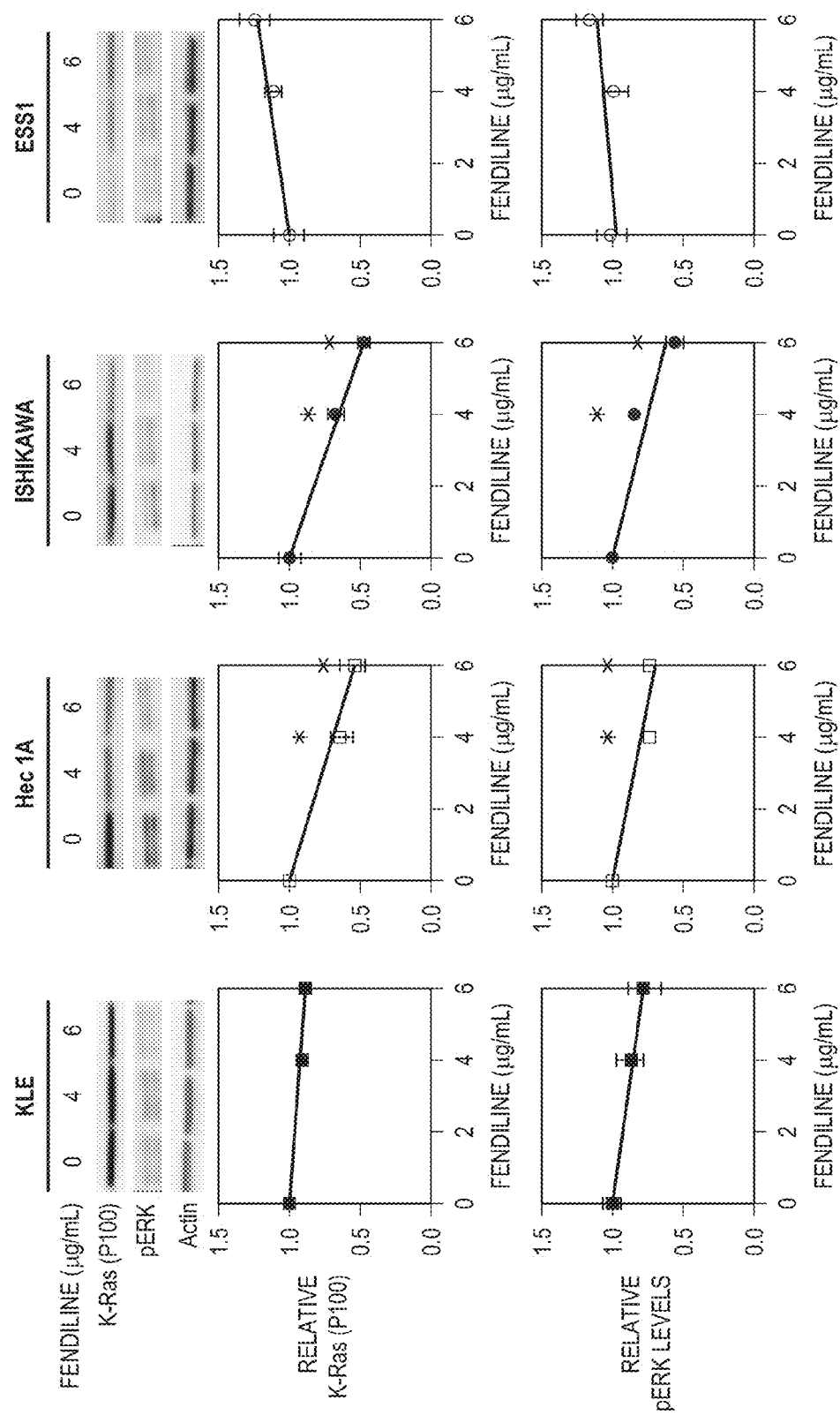

Fendiline Inhibits Proliferation of K-Ras-Transformed Tumor Cell Lines and Tumor Cell Lines that Overexpress Wild Type K-Ras The efficacy of fendiline to inhibit proliferation of a panel of 21 pancreatic, endometrial, lung, and colon tumor cell lines was tested; the panel was chosen to include multiple examples of cell lines that express wild-type and oncogenic mutant K-Ras (FIG. 8A). The results show that regardless of the origin of the tumor, fendiline more potently inhibited the proliferation of tumor cells that express oncogenic mutant K-Ras than tumor cells that express wild-type K-Ras. One exception within the panel was the CaCO-2 colon cancer cell line, which despite being wild type for K-Ras was potently inhibited by fendiline. Interestingly, quantitative immunoblotting showed that K-Ras expression was ~16-fold higher in the CaCO-2 cells than in SNU-C1 cells that were also wild type for K-Ras yet unresponsive to fendiline (FIG. 8B). It is possible that the enhanced K-Ras signaling expected from enhanced K-Ras expression accounts for the sensitivity of CaCO-2 cells to fendiline.

Example 8

Figure 9:
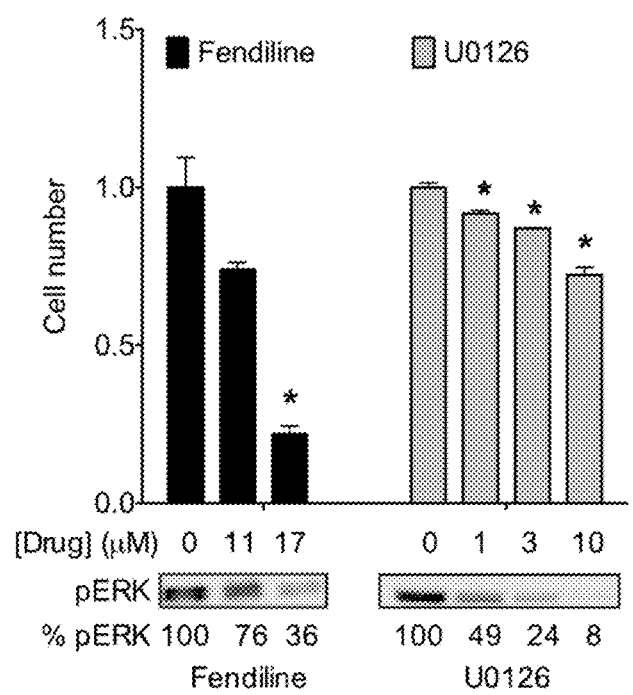
FIG. 9: Illustrates that fendiline is more potent than a MEK inhibitor at blocking proliferation of a tumor cell line expressing oncogenic mutant K-Ras. Hec-1a cells were treated for 48 h with vehicle (DMSO) and various doses of fendiline or U0126. Medium was replaced with fresh U0126 every 24 h, whereas only a single dose of fendiline was added for the duration of the 48 h of incubation. The number of viable cells was quantified (absorbance at 490 nm) using the CellTiter 96 AQueous One Solution cell proliferation assay kit (Promega). The graph shows means±SEMs from 3 independent experiments. Cell numbers were normalized to the corresponding vehicle-treated control. Statistical significance was calculated using Student's t test (*, P<0.05). The pERK levels in cell lysates were quantified using Western blotting, and relative levels are shown.

Fendiline is more potent than a MEK inhibitor at blocking proliferation of a tumor cell line expressing oncogenic mutant K-Ras. Fendiline, by acting at the level of Ras, simultaneously inhibits multiple Ras effector pathways. Therefore the effect of blocking Ras signaling at the level of Ras in blocking K-Ras-driven cell proliferation was tested. K-Ras-transformed Hec1A cells were incubated with increasing concentrations of fendiline or the MEK inhibitor U0126 (FIG. 9) and the effect on cell growth and pERK levels monitored. Interestingly, although U0126 was much more potent than fendiline at inhibiting MAPK activation, fendiline was significantly more potent than U0126 at inhibiting cell proliferation (FIG. 9). Taken together, these results suggest that fendiline inhibits K-Ras-mediated proliferation of cells by blocking more than the Raf-MEK-ERK signaling axis and that concordant inhibition of parallel Ras effector pathways delivers important synergistic effects in abrogating tumor cell growth.

REFERENCES

The following literature citations as well as those cited above are incorporated by reference in their entirety.

REFERENCES

1. Bos J L. ras oncogenes in human cancer: a review. Cancer Res. 1989; 49(17):4682-9.
2. Downward J. Targeting RAS signalling pathways in cancer therapy. Nat Rev Cancer. 2003; 3(1):11-22.
3. Ribas A and Flaherty K T. BRAF targeted therapy changes the treatment paradigm in melanoma. Nat Rev Clin Oncol. 2011; 8(7):426-33.
4. Kefford H A R, Brown M P, Millward M, Infante J R, Long G V, Ouellet D, Curtis M, Lebowitz P F, Falchook G S. Phase I/II study of GSK2118436, a selective inhibitor of oncogenic mutant BRAF kinase, in patients with metastatic melanoma and other solid tumors. J. Clin. Oncol. (Meeting Abstracts) 2010; 28, 8503.
5. Poulikakos P I and Rosen N. Mutant BRAF melanomas—dependence and resistance. Cancer Cell. 2011; 19(1):11-5.
6. Joseph E W, Pratilas C A, Poulikakos P I, Tadi M, Wang W, Taylor B S, Halilovic E, Persaud Y, Xing F, Viale A, Tsai J, Chapman P B, Bollag G, Solit D B and Rosen N. The RAF inhibitor PLX4032 inhibits ERK signaling and tumor cell proliferation in a V600E BRAF-selective manner. Proc Natl Acad Sci USA. 2010; 107(33):14903-8.
7. Flaherty K T, Puzanov I, Kim K B, Ribas A, McArthur G A, Sosman J A, O'Dwyer P J, Lee R J, Grippo J F, Nolop K and Chapman P B. Inhibition of mutated, activated BRAF in metastatic melanoma. N Engl J Med. 2010; 363(9):809-19.
8. Infante J R, Fecher L A, Nallapareddy S, Gordon M S, Flaherty K T, Cox D S, DeMarini D J, Morris S R, Burris H A and Messersmith W A. Safety and efficacy results from the first-in-human study of the oral MEK 1/2 inhibitor GSK1120212. J. Clin. Oncol. (Meeting Abstracts) 2010; 28, 2503.
9. Poulikakos P I and Solit D B. Resistance to MEK inhibitors: should we co-target upstream? Sci. Signal. 2011; 4(166), pe16.
10. Corcoran R B, Settleman J, and Engelman J A. Potential therapeutic strategies to overcome acquired resistance to BRAF or MEK inhibitors in BRAF mutant cancers. Oncotarget. 2011; 2(4): 336-346.
11. Halilovic E and Solit D B. Therapeutic strategies for inhibiting oncogenic BRAF signaling. Curr Opin Pharmacol. 2008; 8(4):419-26.
12. Greger J G, Eastman S D, Zhang V, Bleam M R, Hughes A M, Smitheman K N, Dickerson S H, Laquerre S G, Liu L, and Gilmer T M. Combinations of BRAF, MEK, and PI3K/mTOR Inhibitors Overcome Acquired Resistance to the BRAF Inhibitor GSK2118436 Dabrafenib, Mediated by NRAS or MEK Mutations. Mol Cancer Ther. 2012; 11(4):909-20.
13. Whittaker S, Kirk R, Hayward R, Zambon A, Viros A, Cantarino N, Affolter A, Nourry A, Niculescu-Duvaz D, Springer C, and Marais R. Gatekeeper mutations mediate resistance to BRAF-targeted therapies. Sci Transl Med. 2010; 2(35):35ra41.
14. Nazarian R, Shi H, Wang Q, Kong X, Koya R C, Lee H, Chen Z, Lee M K, Attar N, Sazegar H, Chodon T, Nelson S F, McArthur G, Sosman J A, Ribas A, and Lo R S. Melanomas acquire resistance to B-RAF(V600E) inhibition by RTK or N-RAS upregulation. Nature. 2010; 468(7326):973-7.
15. Wagle N, Emery C, Berger M F, Davis M J, Sawyer A, Pochanard P, Kehoe S M, Johannessen C M, Macconaill L E, Hahn W C, Meyerson M, and Garraway L A. Dissecting Therapeutic Resistance to RAF Inhibition in Melanoma by Tumor Genomic Profiling. J Clin Oncol. 2011; 29(22):3085-96.
16. Heidorn S J, Milagre C, Whittaker S, Nourry A, Niculescu-Duvas I, Dhomen N, Hussain J, Reis-Filho J S, Springer C J, Pritchard C, and Marais R. Kinase-dead BRAF and oncogenic RAS cooperate to drive tumor progression through CRAF. Cell. 2010; 140(2):209-21.
17. Hatzivassiliou G, Song K, Yen I, Brandhuber B J, Anderson D J, Alvarado R, Ludlam M J, Stokoe D, Gloor S L, Vigers G, Morales T, Aliagas I, Liu B, Sideris S, Hoeflich K P, Jaiswal B S, Seshagiri S, Koeppen H, Belvin M, Friedman L S, and Malek S. RAF inhibitors prime wild-type RAF to activate the MAPK pathway and enhance growth. Nature. 2010; 464(7287):431-5.
18. Poulikakos P I, Zhang C, Bollag G, Shokat K M, and Rosen N. RAF inhibitors transactivate RAF dimers and ERK signalling in cells with wild-type BRAF. Nature. 2010; 464(7287):427-30.
19. Omerovic J, Laude A J, and Prior I A. Ras proteins: paradigms for compartmentalised and isoform-specific signalling. Cell Mol Life Sci. 2007; 64(19-20):2575-89.
20. Apolloni A, Prior I A, Lindsay M, Parton R G, and Hancock J F. H-ras but not K-ras traffics to the plasma membrane through the exocytic pathway. Mol Cell Biol. 2000; 20(7):2475-87.
21. Choy E, Chiu V K, Silletti J, Feoktistov M, Morimoto T, Michaelson D, Ivanov I E, Philips M R. Endomembrane trafficking of ras: the CAAX motif targets proteins to the ER and Golgi. Cell. 1999; 98(1):69-80.
22. Hancock J F, Paterson H, and Marshall C J. A polybasic domain or palmitoylation is required in addition to the CAAX motif to localize p21ras to the plasma membrane. Cell. 1990; 63(1):133-9.
23. Choy E, Chiu V K, Silletti J, Feoktistov M, Morimoto T, Michaelson D, Ivanov I E, and Philips M R. Endomembrane trafficking of Ras: the CAAX motif targets proteins to the ER and Golgi. Cell. 1999; 98(1):69-80.
24. Wang G, and Deschenes R J. Plasma membrane localization of Ras requires class C vps proteins and functional mitochondria in *Saccharomyces cerevisiae*. Mol Cell Biol. 2006; 26(8):3243-55.
25. Hancock J F, Magee A I, Childs J E, and Marshall C J. All ras proteins are polyisoprenylated but only some are palmitoylated. Cell. 1989; 57(7):1167-77.

26. Casey P J, Solski P A, Der C J and Buss J E. p21ras is modified by a farnesyl isoprenoid. Proc Natl Acad Sci USA. 1989; 86(21):8323-7.
27. Rowinsky E K. Lately, it occurs to me what a long, strange trip it's been for the farnesyltransferase inhibitors. J Clin Oncol. 2006; 24(19):2981-4.
28. Sebti S M, and Der C J. Opinion: Searching for the elusive targets of farnesyltransferase inhibitors. Nat Rev Cancer. 2003; 3(12):945-51.
29. Hancock J F, Cadwallader K, Paterson H, and Marshall C J. A CAAX or a CAAL motif and a second signal are sufficient for plasma membrane targeting of ras proteins. EMBO J. 1991; 10(13):4033-9.
30. Cox, A. D., Hisaka, M. M., Buss, J. E. & Der, C. J. Specific isoprenoid modification is required for function of normal, but not oncogenic, Ras protein. *Mol Cell Biol* 12, 2606-15 (1992).
31. Panagiotis A. Konstantinopoulos1,2, Michalis V. Karamouzis1 & Athanasios G. Papavassiliou. Nature Reviews Drug Discovery 6, 541-555 (July 2007).
32. Hancock, J. F. Ras proteins: different signals from different locations. *Nat Rev Mol Cell Biol* 4, 373-84 (2003).
33. Hancock, J. F. & Parton, R. G. Ras plasma membrane signalling platforms. *Biochem J* 389, 1-11 (2005).
34. Hancock, J. F., and Prior, I. A. (2005). Electron microscopic imaging of Ras signaling domains. Methods 37, 165-172.
35. Prior, I. A., Muncke, C., Parton, R. G., and Hancock, J. F. (2003). Direct visualization of Ras proteins in spatially distinct cell surface microdomains. J Cell Biol 160, 165-170.
36. Ripley, B. D. (1977). Modelling spatial patterns. J. R. Statist. Soc. B 39, 172-192.
37. Diggle, P. J., J. Mateu, and H. E. Clough. (2000). A comparison between parametric and non-parametric approaches to the analysis of replicated spatial point patterns. Adv. Appl. Probab. 32, 331-343.
38. Plowman, S. J., Muncke, C., Parton, R. G., and Hancock, J. F. (2005). H-ras, K-ras, and inner plasma membrane raft proteins operate in nanoclusters with differential dependence on the actin cytoskeleton. Proc Natl Acad Sci USA 102, 15500-15505.
39. Roy S., Lane A., Yan J., McPherson R., Hancock J. F. (1997) Activity of plasma membrane-recruited Raf-1 is regulated by Ras via the Raf zinc finger. J. Biol. Chem 272:20139-20145.
40. Eisenberg S, Giehl K, Henis Y I, Ehrlich M. J Biol Chem. 2008 Oct. 3; 283(40):27279-88.
41. Bayer, R, Mannhold, R. Fendiline: a review of its basic pharmacological and clinical properties. Pharmatherapeutica 1987; 5: 103-136.
42. Huang C, Huang C, Cheng J, Liu S, Chen I, Tsai J, Chou C, Tseng P, Jan C. Fendiline-evoked [Ca2+]i rises and non-Ca2+-triggered cell death in human oral cancer cells. Hum Exp Toxicol. 2009 January; 28(1):41-8.
43. Lin M C, Jan C R. The anti-anginal drug fendiline elevates cytosolic Ca(2+) in rabbit corneal epithelial cells. Life Sci. 2002 Jul. 19; 71(9):1071-9.
44. Jan C R, Lee K C, Chou K J, Cheng J S, Wang J L, Lo Y K, Chang H T, Tang K Y, Yu C C, Huang J K. Fendiline, an anti-anginal drug, increases intracellular Ca2+ in PC3 human prostate cancer cells. Cancer Chemother Pharmacol. 2001 July; 48(1):37-41.
45. Wang J, Cheng J, Chan R, Tseng L, Chou K, Tang K, Chung Lee K, Lo Y, Wang J, Jan C. The anti-anginal drug fendiline increases intracellular Ca(2+) levels in MG63 human osteosarcoma cells. Toxicol Lett. 2001 Mar. 8; 119(3):227-33.
46. Harding A, Hsu V, Kornfeld K, Hancock J F. J Biol Chem. 2003 Nov. 14; 278(46):45519-27.
47. Hamilton M, Wolfman A. Oncogenic Ha-Ras-dependent mitogen-activated protein kinase activity requires signaling through the epidermal growth factor receptor. J Biol Chem. 1998 Oct. 23; 273(43):28155-62.
48. Weyhenmeyer, R, Fenzl, E, Apecechea, M, Rehm, K D, Dyde, C J, Johnson, K J, et al. Tolerance and pharmacokinetics of oral fendiline. Arzneimittelforschung 1987; 37: 58-62.
49. Zhou Y, Plowman S J, Lichtenberger L M, Hancock J F. The anti-inflammatory drug indometachin alters nanoclustering in synthetic and cell plasma membranes. J Biol Chem. 2010 Nov. 5; 285(45):35188-95.
50. Zhou Y, Cho K J, Plowman S J, Hancock J F. Non-steroidal anti-inflammatory drugs alter the spatiotemporal organization of ras proteins on the plasma membrane. J Biol Chem. 2012 Mar. 19.
51. M. Fivaz, T. Meyer. Reversible intracellular translocation of KRas but not HRas in hippocampal neurons regulated by $C^{a2+}$/calmodulin. J. Cell Biol., 170 (2005), pp. 429-441.
52. C. Figueroa, J. Taylor, A. B. Vojtek. Prenylated Rab acceptor protein is a receptor for prenylated small GTPases. J. Biol. Chem., 276 (2001), pp. 28219-28225.
53. P. Villalonga, C. López-Alcalá, N. Agell et al. Calmodulin binds to K-Ras, but not to H- or N-Ras, and modulates its downstream signaling. Mol. Cell. Biol., 21 (2001), pp. 7345-7354.
54. V. Nancy, I. Callebaut, J. de Gunzburg et al. The δ subunit of retinal rod cGMP phosphodiesterase regulates the membrane association of Ras and Rap GTPases. J. Biol. Chem., 277 (2002), pp. 15076-15084.
55. C. Lopez-Alcalá, B. Alvarez-Moya, N. Agell et al. Identification of essential interacting elements in K-Ras/calmodulin binding and its role in K-Ras localization. J. Biol. Chem., 283 (2008), pp. 10621-10631.
56. M. Hanzal-Bayer, L. Renault, R. C. Hillig et al. The complex of Arl2-GTP and PDE δ: from structure to function. EMBO J., 21 (2002), pp. 2095-2106.
57. R. S. Sidhu, R. R. Clough, R. P. Bhullar. $Ca^{2+}$/calmodulin binds and dissociates K-RasB from membrane. Biochem. Biophys. Res. Commun., 304 (2003), pp. 655-660.
58. Bhagatji P, Leventis R, Rich R, Lin C J, Silvius J R. Multiple cellular proteins modulate the dynamics of K-ras association with the plasma membrane. Biophys J. 2010 Nov. 17; 99(10):3327-35.
59. Chandra A, Grecco H E, Pisupati V, Perera D, Cassidy L, Skoulidis F, Ismail S A, Hedberg C, Hanzal-Bayer M, Venkitaraman A R, Wittinghofer A, Bastiaens P I. The GDI-like solubilizing factor PDEδ sustains the spatial organization and signalling of Ras family proteins. Nat Cell Biol. 2011 Dec. 18; 14(2):148-58Shalom-Feuerstein, S. J. Plowman, Y. Kloog et al. K-ras nanoclustering is subverted by overexpression of the scaffold protein galectin-3. Cancer Res., 68 (2008), pp. 6608-6616.
60. Gigl, G, Hartweg, D, Sanchez-Delgado, E, Metz, G, Gietzen, K. Calmodulin antagonism: a pharmacological approach for the inhibition of mediator release from mast cells. Cell Calcium 1987; 8: 327-344.

61. Orosz, F, Christova, T Y, Ovadi, J. Functional in vitro test of calmodulin antagonism: effect of drugs on interaction between calmodulin and glycolytic enzymes. Mol Pharmacol 1988; 33: 678-682.
62. G. Elad, A. Paz, Y. Kloog et al. Targeting of K-Ras 4B by S-trans,trans-farnesyl thiosalicylic acid. Biochim. Biophys. Acta, 1452 (1999), pp. 228-242.
63. Lückhoff A, Bohnert M, Busse R. Effects of the calmodulin antagonists fendiline and calmidazolium on aggregation, secretion of ATP, and internal calcium in washed human platelets. Naunyn Schmiedebergs Arch Pharmacol. 1991 January; 343(1):96-101.
64. Kukovetz W R, Brunner F, Beubler E, Weyhenmeyer R, Lohaus R, Grob M, Mayer D. Single dose pharmacokinetics of fendiline in humans. Eur J Drug Metab Pharmacokinet. 1982; 7(2):105-10;
65. Weyhenmeyer R, Fenzl E, Apecechea M, Rehm K D, Dyde C J, Johnson K J, Friedel R. Tolerance and pharmacokinetics of oral fendiline. Arzneimittelforschung. 1987 January; 37(1):58-62).

Without further elaboration, it is believed that one skilled in the art can, using the description herein, utilize the present methods to its fullest extent. The embodiments described herein are to be construed as illustrative and not as constraining the remainder of the disclosure in any way whatsoever. While preferred embodiments have been shown and described, many variations and modifications thereof can be made by one skilled in the art without departing from the spirit and teachings of the presently disclosed methods. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they are consistent with the present disclosure set forth herein.

What is claimed is:

1. A method of treating a K-ras mediated disorder in a patient in need thereof, said method comprising:
    administering to the patient a therapeutically effective amount of fendiline; fendiline HCl or combination thereof that inhibits K-ras signaling by blocking the association of the K-ras protein with plasma membrane, and wherein said disorder is selected from: leukemia, colorectal cancer, pancreatic cancer, lung cancer or endometrial cancer.
2. The method of claim 1, wherein fendiline or fendiline HCl is used in combination with at least one other chemotherapeutic compound in a combination therapy.
3. The method of claim 1, wherein said disorder is characterized by the presence of a mutant K-ras oncogene.
4. The method of claim 1, wherein said fendiline; fendiline HCl or combination thereof inhibits K-ras-dependent RAF-MAPK and PI3K-AKT signaling in said leukemia, colorectal cancer, pancreatic cancer, lung cancer or endometrial cancer.
5. The method of claim 1 wherein said administering is by one of: intravenous administering, subcutaneous administering, intramuscular administering, intraperitoneal administering, intrathecal administering or topical administering.

* * * * *